United States Patent
Boye et al.

(10) Patent No.: US 9,375,491 B2
(45) Date of Patent: Jun. 28, 2016

(54) CHIMERIC PROMOTER FOR CONE PHOTORECEPTOR TARGETED GENE THERAPY

(71) Applicant: UNIVERSITY OF FLORIDA RESEARCH FOUNDATION, INC., Gainesville, FL (US)

(72) Inventors: Sanford Leon Boye, Gainesville, FL (US); Frank Markus Dyka, Gainesville, FL (US); William W. Hauswirth, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/354,471

(22) PCT Filed: Oct. 29, 2012

(86) PCT No.: PCT/US2012/062478
§ 371 (c)(1),
(2) Date: Apr. 25, 2014

(87) PCT Pub. No.: WO2013/063601
PCT Pub. Date: May 2, 2013

(65) Prior Publication Data
US 2014/0275231 A1    Sep. 18, 2014

Related U.S. Application Data

(60) Provisional application No. 61/552,975, filed on Oct. 28, 2011.

(51) Int. Cl.
*A61K 48/00* (2006.01)
*C12N 15/86* (2006.01)

(52) U.S. Cl.
CPC .............. *A61K 48/005* (2013.01); *C12N 15/86* (2013.01); *C12N 2750/14143* (2013.01); *C12N 2830/008* (2013.01); *C12N 2830/85* (2013.01)

(58) Field of Classification Search
None
See application file for complete search history.

(56) References Cited

U.S. PATENT DOCUMENTS

| | | | |
|---|---|---|---|
| 5,986,174 A | 11/1999 | Barbour et al. | |
| 6,080,914 A | 6/2000 | Conner | |
| 6,106,826 A | 8/2000 | Brandt et al. | |
| 6,165,781 A | 12/2000 | Carter et al. | |
| 6,204,251 B1 | 3/2001 | Cuthbertson | |
| 6,461,606 B1 | 10/2002 | Flotte et al. | |
| 6,660,514 B1 | 12/2003 | Zolotukhin et al. | |
| 6,967,018 B2 | 11/2005 | Zolotukhin et al. | |
| 7,094,604 B2 | 8/2006 | Snyder et al. | |
| 8,137,692 B2 | 3/2012 | Timms | |

FOREIGN PATENT DOCUMENTS

| | | |
|---|---|---|
| WO | WO-98/48027 | 10/1998 |
| WO | WO 2008/065430 A2 | 6/2008 |
| WO | WO-2011/034947 | 3/2011 |

OTHER PUBLICATIONS

CNGB3 [*Homo sapiens*]; cyclic nucleotide-gated cation channel beta-3 [*Homo sapiens*]; NCBI; www.ncbi.nlm.nih.gov/protein/116642889?sat=14&satkey=51978; pp. 1-4, available Apr. 19, 2010.*

Alexander, J.J., et al., "Restoration of cone vision in a mouse model of achromatopsia," *Nature Medicine*, Jun. 2007, vol. 13, No. 6, pp. 685-687.

Carvalho, L.S., et al., "Long-term and age-dependent restoration of visual function in a mouse model of CNGB3-associated achromatopsia following gene therapy," *Human Molecular Genetics*, 2011, vol. 20, No. 16, pp. 3161-3175.

Daniele, L.L., et al., "Cone-like morphological, molecular, and electrophysiological features of the photoreceptors of the NRL knockout mouse," *Investigative Ophthalmology & Visual Science*, Jun. 2005, vol. 46, No. 6, pp. 2156-2167.

Fong, S.L., et al., "Characterization and Comparative Structural Features of the Gene for Human Interstitial Retinol-binding Protein," *Journal of Biological Chemistry*, Mar. 5, 1990, vol. 265, No. 7, pp. 3648-3653.

Fong, S.L., et al., "Characterization of a transgenic mouse line lacking photoreceptor development within the ventral retina," *Experimental Eye Research*, Oct. 2005, vol. 81, No. 4, pp. 376-388.

Glushakova, L.G., et al., "Human blue-opsin promoter preferentially targets reporter gene expression to rat s-cone photoreceptors," *Investigative Ophthalmology & Visual Science*, Aug. 2006, vol. 47, No. 8, pp. 3505-3513.

Komáromy, A.M., et al., "Gene therapy rescues cone function in congenital achromatopsia," *Human Molecular Genetics*, 2010, vol. 19, No. 13, pp. 2581-2593.

(Continued)

*Primary Examiner* — Antonio Galisteo Gonzalez
(74) *Attorney, Agent, or Firm* — Wolf, Greenfield & Sacks, P.C.

(57) ABSTRACT

The subject invention concerns materials and methods for providing for cone cell specific expression of a polynucleotide in a human or animal. One aspect of the invention concerns a polynucleotide promoter sequence that directs expression of an operably linked polynucleotide in cone cells. In one embodiment, a polynucleotide of the invention comprises a nucleotide sequence of an interphotoreceptor retinoid-binding protein (IRBP) gene that is positioned upstream of a promoter nucleotide sequence of a cone transducin alpha-subunit (GNAT2) gene. Another aspect of the subject invention concerns methods for expressing a selected polynucleotide in cone cells. The selected polynucleotide can be provided in a polynucleotide of the invention wherein the selected polynucleotide is operably linked to a polynucleotide promoter sequence of the invention. In one embodiment, the selected polynucleotide sequence is provided in a polynucleotide vector of the invention. The vector comprising the selected polynucleotide is then introduced into a cell. The selected polynucleotide is expressed only in cone cells, with very little, if any, expression in rods or other cells. A selected polynucleotide can be one that encodes, for example, a therapeutic protein or a functional protein that is defective or underexpressed in the targeted cone cells.

5 Claims, 17 Drawing Sheets

(56) References Cited

OTHER PUBLICATIONS

Komáromy, A.M., et al., "Targeting gene expression to cones with human cone opsin promoters in recombinant AAV," *Gene Therapy*, 2008, vol. 15, No. 14, pp. 1049-1055.

Li, A., et al., "Retinoic acid upregulates cone arrestin expression in restinoblastoma cells through a Cis element in the distal promoter region," *Investigative Ophthalmology & Visual Science*, 2002, vol. 43, No. 5, pp. 1375-1383.

Mancuso, K., et al., "Gene therapy for red-green colour blindness in adult primates," *Nature*, Oct. 8, 2009, vol. 461, No. 7265, pp. 784-787.

Mears, A.J., et al., "Nrl is required for rod photoreceptor development," *Nature Genetics*, 2001, vol. 29, No. 4, pp. 447-452.

Michalakis, S., et al., "Restoration of cone vision in the CNGA3-/- mouse model of congenital complete lack of cone photoreceptor function," *Molecular Therapy*, Dec. 2010, vol. 18, No. 12, pp. 2057-2063.

Morris, T.A., et al., "Characterization of the Gene Encoding Human Cone Transducin α-Subunit (GNAT2)," *Genomics*, 1993, vol. 17, No. 2, pp. 442-448.

Nikonov, S.S., et al., "Photoreceptors of NRL-/- mice coexpress functional S- and M-cone opsins having distinct inactivation mechanisms," *Journal of General Physiology*, Mar. 2005, vol. 125, No. 3, pp. 287-304.

Pang, J.J. et al., "Achromatopsia as a potential candidate for gene therapy," in Retinal Degenerativ Disease, Anderson et al., Eds., 2010, Series vol. 664, Chapter 73, pp. 639-646.

Ying, S., et al., "A CAT reporter construct containing 277bp GNAT2 promoter and 214bp IRBP enhancer is specifically expressed by cone photoreceptor cells in transgenic mice," *Current Eye Research*, Aug. 1998, vol. 17, No. 8, pp. 777-782.

Ying, S., et al., "Retinal degeneration in cone photoreceptor cell-ablated transgenic mice," *Molecular Vision*, Jun. 24, 2000, vol. 6, pp. 101-108.

International Search Report and Written Opinion for Application No. PCT/US2012/062478 mailed Feb. 27, 2013.

International Preliminary Report on Patentability for Application No. PCT/US2012/062478 mailed May 8, 2014.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Beltz et al., Isolation of multigene families and determination of homologies by filter hybridization methods. Methods Enzymol. 1983;100:266-85.

Felgner et al., Lipofection: a highly efficient, lipid-mediated DNA-transfection procedure. Proc Natl Acad Sci U S A. Nov. 1987;84(21):7413-7.

Genbank Accession No. AAF86274.1. Kohl et al., Aug. 29, 2000. 2 pages.

Genbank Accession No. AAH96298. Strausberg et al., Jan. 4, 2007. 2 pages.

Genbank Accession No. AAH96300.1. Strausberg et al., Jan. 4, 2007. 2 pages.

Genbank Accession No. NM_019098.4. Doucette et al., Mar. 15, 2015. 6 pages.

Genbank Accession No. NP_061971.3. Doucette et al., Mar. 15, 2015. 4 pages.

Genbank Accession No. Q16281.2. Ota et al., Dec. 9, 2015. 19 pages.

Karlin et al., Applications and statistics for multiple high-scoring segments in molecular sequences. Proc Natl Acad Sci U S A. Jun. 15, 1993;90(12):5873-7.

Karlin et al., Methods for assessing the statistical significance of molecular sequence features by using general scoring schemes. Proc Natl Acad Sci U S A. Mar. 1990;87(6):2264-8.

May et al., In vitro comparison studies of truncated rhodopsin promoter fragments from various species in human cell lines. Clin Experiment Ophthalmol. Oct. 2003;31(5):445-50.

Nicoud et al., Devolopment of photoreceptor-specific promoters and their utility to investigate EIAV lentiviral vector mediated gene transfer to photoreceptors. J Gene Med. Dec. 2007;9(12):1015-23.

\* cited by examiner

S-opsin   M-opsin

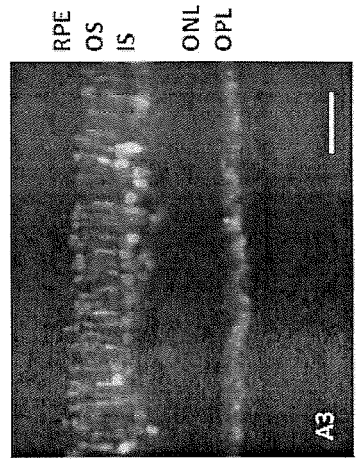
FIG. 11A-3 merged
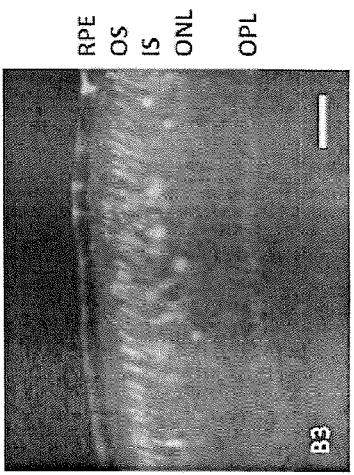
FIG. 11B-3
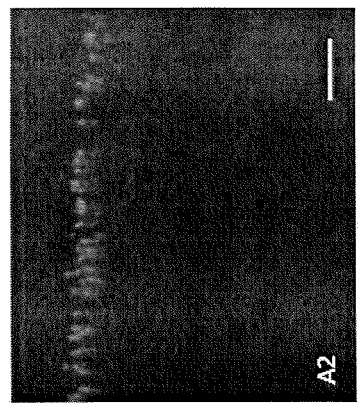
FIG. 11A-2 M+S opsin
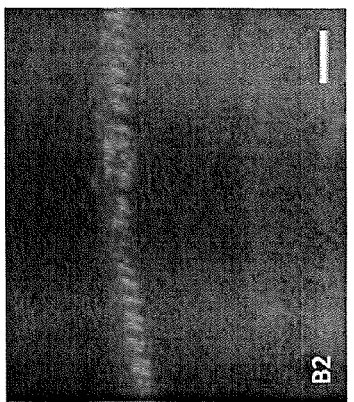
FIG. 11B-2
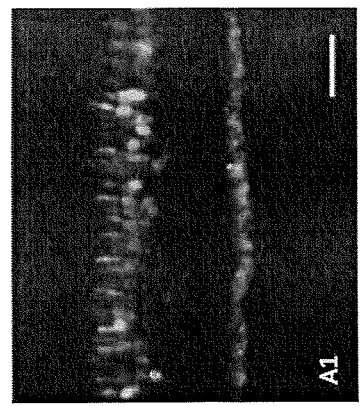
FIG. 11A-1 GFP
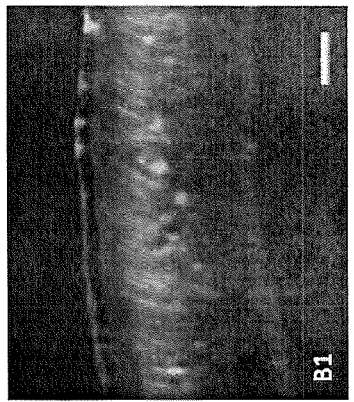
FIG. 11B-1

SEQUENCE LISTING

```
<160> NUMBER OF SEQ ID NOS: 6

<210> SEQ ID NO 1
<211> LENGTH: 506
<212> TYPE: DNA
<213> ORGANISM: Artificial Sequence
<220> FEATURE:
<223> OTHER INFORMATION: IRBP/GNAT chimeric promoter
```

<400> SEQUENCE: 1

```
ggcccaggct tcccagcagg gctaaggata tgcaaggagt gcattcatcc ggaggtgttg    60
gcagcatccc agccccaccc cattctcatc gtaaatcagg ctcacttcca ttggctgcat   120
acggtggagt gatgtgacca tatgtcactt gagcattaca caaatcctaa tgagctaaaa   180
atatgtttgt tttagctaat tgacctcttt ggccactagt gttgctagcg tgcatcctat   240
ccttccgtca gaacccagca gatcatttcc ctagttatag aaacatttga gtctttaccc   300
cttgccatat tgacaaagct cttaattggc ttgacctatc acattgctag atataaaggc   360
tacaatccct agactaagaa gtaggtctcc agttgaagta gggagtctca gtcaatgtag   420
gcagagtaca agaccctaca gcctgctctc tcacctgcca tcgtacagac cagcttttag   480
gggagccaag ttgggatact caatcc                                        506
```

<210> SEQ ID NO 2
<211> LENGTH: 214
<212> TYPE: DNA
<213> ORGANISM: Homo sapiens

<400> SEQUENCE: 2

```
ggcccaggct tcccagcagg gctaaggata tgcaaggagt gcattcatcc ggaggtgttg    60
gcagcatccc agccccaccc cattctcatc gtaaatcagg ctcacttcca ttggctgcat   120
acggtggagt gatgtgacca tatgtcactt gagcattaca caaatcctaa tgagctaaaa   180
atatgtttgt tttagctaat tgacctcttt ggcc                               214
```

<210> SEQ ID NO 3
<211> LENGTH: 277
<212> TYPE: DNA
<213> ORGANISM: Homo sapiens

<400> SEQUENCE: 3

```
gtgcatccta tccttccgtc agaacccagc agatcatttc cctagttata gaaacatttg    60
agtctttacc ccttgccata ttgacaaagc tcttaattgg cttgacctat cacattgcta   120
gatataaagg ctacaatccc tagactaaga agtaggtctc cagttgaagt agggagtctc   180
agtcaatgta ggcagagtac aagaccctac agcctgctct ctcacctgcc atcgtacaga   240
ccagctttta ggggagccaa gttgggatac tcaatcc                            277
```

<210> SEQ ID NO 4
<211> LENGTH: 524
<212> TYPE: DNA
<213> ORGANISM: Artificial sequence
<220> FEATURE:
<223> OTHER INFORMATION: IRBP/GNAT2 chimeric promoter

<400> SEQUENCE: 4

```
gaattcggcc caggcttccc agcagggcta aggatatgca aggagtgcat tcatccggag    60
gtgttggcag catcccagcc ccaccccatt ctcatcgtaa atcaggctca cttccattgg   120
ctgcatacgg tggagtgatg tgaccatatg tcacttgagc attacacaaa tcctaatgag   180
ctaaaaatat gtttgtttta gctaattgac ctctttggcc actagtgttg ctagcgtgca   240
tcctatcctt ccgtcagaac ccagcagatc atttccctag ttatagaaac atttgagtct   300
ttaccccttg ccatattgac aaagctctta attggcttga cctatcacat tgctagatat   360
aaaggctaca atccctagac taagaagtag gtctccagtt gaagtaggga gtctcagtca   420
```

```
atgtaggcag agtacaagac cctacagcct gctctctcac ctgccatcgt acagaccagc    480 tttagggga gccaagttgg gatactcaat cctctagact cgag                      524
```

<210> SEQ ID NO 5
<211> LENGTH: 809
<212> TYPE: PRT
<213> ORGANISM: Homo sapiens

<400> SEQUENCE: 5

```
Met Phe Lys Ser Leu Thr Lys Val Asn Lys Val Pro Ile Gly Glu
1               5                   10                  15

Asn Asn Glu Asn Glu Gln Ser Ser Arg Arg Asn Glu Glu Gly Ser His
            20                  25                  30

Pro Ser Asn Gln Ser Gln Gln Thr Thr Ala Gln Glu Glu Asn Lys Gly
        35                  40                  45

Glu Glu Lys Ser Leu Lys Thr Lys Ser Thr Pro Val Thr Ser Glu Glu
    50                  55                  60

Pro His Thr Asn Ile Gln Asp Lys Leu Ser Lys Lys Asn Ser Ser Gly
65                  70                  75                  80

Asp Leu Thr Thr Asn Pro Asp Pro Gln Asn Ala Ala Glu Pro Thr Gly
                85                  90                  95

Thr Val Pro Glu Gln Lys Glu Met Asp Pro Gly Lys Glu Gly Pro Asn
            100                 105                 110

Ser Pro Gln Asn Lys Pro Pro Ala Ala Pro Val Ile Asn Glu Tyr Ala
        115                 120                 125

Asp Ala Gln Leu His Asn Leu Val Lys Arg Met Arg Gln Arg Thr Ala
    130                 135                 140

Leu Tyr Lys Lys Lys Leu Val Glu Gly Asp Leu Ser Ser Pro Glu Ala
145                 150                 155                 160

Ser Pro Gln Thr Ala Lys Pro Thr Ala Val Pro Pro Val Lys Glu Ser
                165                 170                 175

Asp Asp Lys Pro Thr Glu His Tyr Tyr Arg Leu Leu Trp Phe Lys Val
            180                 185                 190

Lys Lys Met Pro Leu Thr Glu Tyr Leu Lys Arg Ile Lys Leu Pro Asn
        195                 200                 205

Ser Ile Asp Ser Tyr Thr Asp Arg Leu Tyr Leu Leu Trp Leu Leu Leu
    210                 215                 220

Val Thr Leu Ala Tyr Asn Trp Asn Cys Cys Phe Ile Pro Leu Arg Leu
225                 230                 235                 240

Val Phe Pro Tyr Gln Thr Ala Asp Asn Ile His Tyr Trp Leu Ile Ala
                245                 250                 255

Asp Ile Ile Cys Asp Ile Ile Tyr Leu Tyr Asp Met Leu Phe Ile Gln
            260                 265                 270

Pro Arg Leu Gln Phe Val Arg Gly Gly Asp Ile Ile Val Asp Ser Asn
        275                 280                 285

Glu Leu Arg Lys His Tyr Arg Thr Ser Thr Lys Phe Gln Leu Asp Val
    290                 295                 300

Ala Ser Ile Ile Pro Phe Asp Ile Cys Tyr Leu Phe Gly Phe Asn
305                 310                 315                 320

Pro Met Phe Arg Ala Asn Arg Met Leu Lys Tyr Thr Ser Phe Phe Glu
                325                 330                 335

Phe Asn His His Leu Glu Ser Ile Met Asp Lys Ala Tyr Ile Tyr Arg
            340                 345                 350

Val Ile Arg Thr Thr Gly Tyr Leu Leu Phe Ile Leu His Ile Asn Ala
```

-continued

```
            355                 360                 365
Cys Val Tyr Tyr Trp Ala Ser Asn Tyr Glu Ile Gly Thr Thr Arg
    370                 375                 380
Trp Val Tyr Asp Gly Glu Gly Asn Glu Tyr Leu Arg Cys Tyr Tyr Trp
385                 390                 395                 400
Ala Val Arg Thr Leu Ile Thr Ile Gly Gly Leu Pro Glu Pro Gln Thr
                405                 410                 415
Leu Phe Glu Ile Val Phe Gln Leu Leu Asn Phe Phe Ser Gly Val Phe
            420                 425                 430
Val Phe Ser Ser Leu Ile Gly Gln Met Arg Asp Val Ile Gly Ala Ala
            435                 440                 445
Thr Ala Asn Gln Asn Tyr Phe Arg Ala Cys Met Asp Asp Thr Ile Ala
            450                 455                 460
Tyr Met Asn Asn Tyr Ser Ile Pro Lys Leu Val Gln Lys Arg Val Arg
465                 470                 475                 480
Thr Trp Tyr Glu Tyr Thr Trp Asp Ser Gln Arg Met Leu Asp Glu Ser
                485                 490                 495
Asp Leu Leu Lys Thr Leu Pro Thr Thr Val Gln Leu Ala Leu Ala Ile
            500                 505                 510
Asp Val Asn Phe Ser Ile Ile Ser Lys Val Asp Leu Phe Lys Gly Cys
            515                 520                 525
Asp Thr Gln Met Ile Tyr Asp Met Leu Leu Arg Leu Lys Ser Val Leu
            530                 535                 540
Tyr Leu Pro Gly Asp Phe Val Cys Lys Gly Glu Ile Gly Lys Glu
545                 550                 555                 560
Met Tyr Ile Ile Lys His Gly Glu Val Gln Val Leu Gly Gly Pro Asp
                565                 570                 575
Gly Thr Lys Val Leu Val Thr Leu Lys Ala Gly Ser Val Phe Gly Glu
            580                 585                 590
Ile Ser Leu Leu Ala Ala Gly Gly Asn Arg Arg Thr Ala Asn Val
            595                 600                 605
Val Ala His Gly Phe Ala Asn Leu Leu Thr Leu Asp Lys Lys Thr Leu
            610                 615                 620
Gln Glu Ile Leu Val His Tyr Pro Asp Ser Glu Arg Ile Leu Met Lys
625                 630                 635                 640
Lys Ala Arg Val Leu Leu Lys Gln Lys Ala Lys Thr Ala Glu Ala Thr
                645                 650                 655
Pro Pro Arg Lys Asp Leu Ala Leu Leu Phe Pro Pro Lys Glu Glu Thr
            660                 665                 670
Pro Lys Leu Phe Lys Thr Leu Leu Gly Gly Thr Gly Lys Ala Ser Leu
            675                 680                 685
Ala Arg Leu Leu Lys Leu Lys Arg Glu Gln Ala Ala Gln Lys Lys Glu
            690                 695                 700
Asn Ser Glu Gly Gly Glu Glu Gly Lys Glu Asn Glu Asp Lys Gln
705                 710                 715                 720
Lys Glu Asn Glu Asp Lys Gln Lys Glu Asn Glu Asp Lys Gly Lys Glu
                725                 730                 735
Asn Glu Asp Lys Asp Lys Gly Arg Glu Pro Glu Lys Pro Leu Asp
            740                 745                 750
Arg Pro Glu Cys Thr Ala Ser Pro Ile Ala Val Glu Glu Pro His
            755                 760                 765
Ser Val Arg Arg Thr Val Leu Pro Arg Gly Thr Ser Arg Gln Ser Leu
            770                 775                 780
```

Ile Ile Ser Met Ala Pro Ser Ala Glu Gly Gly Glu Glu Val Leu Thr
785                 790                 795                 800

Ile Glu Val Lys Glu Lys Ala Lys Gln
            805

<210> SEQ ID NO 6
<211> LENGTH: 694
<212> TYPE: PRT
<213> ORGANISM: Homo sapiens

<400> SEQUENCE: 6

Met Ala Lys Ile Asn Thr Gln Tyr Ser His Pro Ser Arg Thr His Leu
1               5                   10                  15

Lys Val Lys Thr Ser Asp Arg Asp Leu Asn Arg Ala Glu Asn Gly Leu
            20                  25                  30

Ser Arg Ala His Ser Ser Ser Glu Glu Thr Ser Ser Val Leu Gln Pro
        35                  40                  45

Gly Ile Ala Met Glu Thr Arg Gly Leu Ala Asp Ser Gly Gln Gly Ser
    50                  55                  60

Phe Thr Gly Gln Gly Ile Ala Arg Leu Ser Arg Leu Ile Phe Leu Leu
65                  70                  75                  80

Arg Arg Trp Ala Ala Arg His Val His His Gln Asp Gln Gly Pro Asp
                85                  90                  95

Ser Phe Pro Asp Arg Phe Arg Gly Ala Glu Leu Lys Glu Val Ser Ser
            100                 105                 110

Gln Glu Ser Asn Ala Gln Ala Asn Val Gly Ser Gln Glu Pro Ala Asp
        115                 120                 125

Arg Gly Arg Ser Ala Trp Pro Leu Ala Lys Cys Asn Thr Asn Thr Ser
    130                 135                 140

Asn Asn Thr Glu Glu Glu Lys Lys Thr Lys Lys Lys Asp Ala Ile Val
145                 150                 155                 160

Val Asp Pro Ser Ser Asn Leu Tyr Tyr Arg Trp Leu Thr Ala Ile Ala
                165                 170                 175

Leu Pro Val Phe Tyr Asn Trp Tyr Leu Leu Ile Cys Arg Ala Cys Phe
            180                 185                 190

Asp Glu Leu Gln Ser Glu Tyr Leu Met Leu Trp Leu Val Leu Asp Tyr
        195                 200                 205

Ser Ala Asp Val Leu Tyr Val Leu Asp Val Leu Val Arg Ala Arg Thr
    210                 215                 220

Gly Phe Leu Glu Gln Gly Leu Met Val Ser Asp Thr Asn Arg Leu Trp
225                 230                 235                 240

Gln His Tyr Lys Thr Thr Thr Gln Phe Lys Leu Asp Val Leu Ser Leu
                245                 250                 255

Val Pro Thr Asp Leu Ala Tyr Leu Lys Val Gly Thr Asn Tyr Pro Glu
            260                 265                 270

Val Arg Phe Asn Arg Leu Leu Lys Phe Ser Arg Leu Phe Glu Phe Phe
        275                 280                 285

Asp Arg Thr Glu Thr Arg Thr Asn Tyr Pro Asn Met Phe Arg Ile Gly
    290                 295                 300

Asn Leu Val Leu Tyr Ile Leu Ile Ile His Trp Asn Ala Cys Ile
305                 310                 315                 320

Tyr Phe Ala Ile Ser Lys Phe Ile Gly Phe Gly Thr Asp Ser Trp Val
                325                 330                 335

Tyr Pro Asn Ile Ser Ile Pro Glu His Gly Arg Leu Ser Arg Lys Tyr

```
                    340             345             350
Ile Tyr Ser Leu Tyr Trp Ser Thr Leu Thr Leu Thr Thr Ile Gly Glu
            355                 360                 365

Thr Pro Pro Val Lys Asp Glu Glu Tyr Leu Phe Val Val Val Asp
    370                 375                 380

Phe Leu Val Gly Val Leu Ile Phe Ala Thr Ile Val Gly Asn Val Gly
385                 390                 395                 400

Ser Met Ile Ser Asn Met Asn Ala Ser Arg Ala Glu Phe Gln Ala Lys
                405                 410                 415

Ile Asp Ser Ile Lys Gln Tyr Met Gln Phe Arg Lys Val Thr Lys Asp
            420                 425                 430

Leu Glu Thr Arg Val Ile Arg Trp Phe Asp Tyr Leu Trp Ala Asn Lys
            435                 440                 445

Lys Thr Val Asp Glu Lys Glu Val Leu Lys Ser Leu Pro Asp Lys Leu
    450                 455                 460

Lys Ala Glu Ile Ala Ile Asn Val His Leu Asp Thr Leu Lys Lys Val
465                 470                 475                 480

Arg Ile Phe Gln Asp Cys Glu Ala Gly Leu Leu Val Glu Leu Val Leu
                485                 490                 495

Lys Leu Arg Pro Thr Val Phe Ser Pro Gly Asp Tyr Ile Cys Lys Lys
            500                 505                 510

Gly Asp Ile Gly Lys Glu Met Tyr Ile Ile Asn Glu Gly Lys Leu Ala
        515                 520                 525

Val Val Ala Asp Asp Gly Val Thr Gln Phe Val Val Leu Ser Asp Gly
        530                 535                 540

Ser Tyr Phe Gly Glu Ile Ser Ile Leu Asn Ile Lys Gly Ser Lys Ser
545                 550                 555                 560

Gly Asn Arg Arg Thr Ala Asn Ile Arg Ser Ile Gly Tyr Ser Asp Leu
                565                 570                 575

Phe Cys Leu Ser Lys Asp Asp Leu Met Glu Ala Leu Thr Glu Tyr Pro
            580                 585                 590

Glu Ala Lys Lys Ala Leu Glu Glu Lys Gly Arg Gln Ile Leu Met Lys
            595                 600                 605

Asp Asn Leu Ile Asp Glu Glu Leu Ala Arg Ala Gly Ala Asp Pro Lys
    610                 615                 620

Asp Leu Glu Glu Lys Val Glu Gln Leu Gly Ser Ser Leu Asp Thr Leu
625                 630                 635                 640

Gln Thr Arg Phe Ala Arg Leu Leu Ala Glu Tyr Asn Ala Thr Gln Met
                645                 650                 655

Lys Met Lys Gln Arg Leu Ser Gln Leu Glu Ser Gln Val Lys Gly Gly
            660                 665                 670

Gly Asp Lys Pro Leu Ala Asp Gly Glu Val Pro Gly Asp Ala Thr Lys
        675                 680                 685

Thr Glu Asp Lys Gln Gln
        690
```

CHIMERIC PROMOTER FOR CONE PHOTORECEPTOR TARGETED GENE THERAPY

CROSS-REFERENCE TO RELATED APPLICATIONS

This application is the National Stage of International Application No. PCT/US2012/062478, filed Oct. 29, 2012, which claims the benefit of U.S. Provisional Application Serial No. 61/552,975, filed Oct. 28, 2011, each of which is hereby incorporated by reference herein in its entirety, including any figures, tables, nucleic acid sequences, amino acid sequences, or drawings.

GOVERNMENT SUPPORT

This invention was made with government support under grant number EY008571 awarded by the National Institutes of Health. The government has certain rights in the invention.

The Sequence Listing for this application is labeled "2C36312.TXT" which was created on Apr. 23, 2014 and is 16 KB. The entire contents of the sequence listing is incorporated herein by reference in its entirety.

BACKGROUND OF THE INVENTION

Cone photoreceptors are responsible for high acuity, central daylight and color vision. In humans there are 3 distinct subclasses of cone photoreceptors, each named for the specific wavelength of light to which they respond. Spectral sensitivity it mediated by the specific form of cone opsin that each cone subclass expresses. Cones that express S opsin respond to short wavelength light (blue: 420-440 nm) are referred to as "S" cones. Cones that respond to medium wavelength light (green: 534-545 nm) express M opsin and are referred to as "M" cones, and finally cones that express L opsin respond to long wavelength light (red: 564-580 nm) are referred to as "L" cones. Gene therapy based treatments for a number of diseases affecting cone photoreceptors are currently under development. One such disease, Achromatopsia, is characterized by an inability to see color, blindness in full sunlight (or at high light levels) and very poor visual acuity. Although congenital achomatopsia (ACHM) is a relatively rare disorder, it is a good target for gene therapy as the causative genes are known and proof-of-concept gene replacement studies in animal models have clearly shown success (Pang et al. (2010)). ACHM affects all classes of photoreceptors, including S cones. Recent evidence from case studies of patients with ACHM suggests that ACHM is progressive, with cones degenerating over time. Therefore, early intervention with a therapy that targets all cone photoreceptors would be ideal. Additionally, any disease that broadly affects cone photoreceptors, such as progressive cone dystrophy, would benefit from a gene therapy approach that was capable of targeting all cones.

In order to effectively and safely deliver genes to cone photoreceptors of ACHM affected individuals, gene therapy vectors must utilize promoters that meet the following criteria 1) the promoter must drive transgene expression both efficiently and selectively in cones, with no off-target expression in rod photoreceptors or other non-photoreceptor cell types, such as the retinal pigment epithelium (RPE), 2) the promoter must be capable of driving gene expression in all subclasses of cone photoreceptors, and 3) the promoter should be small, thereby allowing for sufficient carrying capacity of the vector to accommodate transgene DNA. To date, cone targeting promoters used in gene therapy proof-of-concept experiments of ACHM have been deficient in one or more of these criteria. In gene therapy studies by Alexander et al. (2007) and Komaromy et al. (2010) a 2100 base pair version of the human red/green opsin promoter (PR 2.1) was used to drive therapeutic transgene expression. In humans, the genes for M and L opsin are arranged in tandem on the X chromosome and therefore share a common promoter. In mouse, expression was limited to cones and some rod photoreceptors (Alexander et al. (2007)). In dogs, expression was limited to M and L cones (Komaromy et al. (2010)). While highly selective for M/L cone photoreceptors in dogs, PR2.1 mediated expression was not observed in S cones. Additionally the PR2.1 promoter is relatively large and in the case of the CNGB3 form of ACHM, AAV vectors (packaging size limitation of <5 KB) are barely able to accommodate promoter and cDNA, and this in turn reduces vector manufacturing efficiency. Promoters isolated from either the human or mouse blue cone (S) opsin gene have also been characterized for AAV mediate expression and gene replacement studies in ACHM animal models. These promoters are from nearly identical regions of the blue cone opsin genes of each respective species (i.e., are homologous). In rat, the human blue cone opsin promoter (HB569) drove reporter gene expression in all cone subclasses; however expression was weaker relative to the PR2.1 promoter (Glushakova et al. (2006)). In dog, HB569 performed poorly in terms of both specificity and efficiency, with relatively few L/M cones expressing transgene, rods and RPE positive for expression and overall weak expression. The mouse blue cone opsin promoter (mBP) has been tested in the context of gene replacement for the CNGA3 form of ACHM and performed well, however the likelihood is that like the closely related HB569, this promoter, will perform poorly in higher order mammals, such as dog and human. Finally, both human and mouse cone arrestin promoters have been utilized in AAV transduction experiments and later in gene replacement studies in ACHM animal models. As with the blue cone promoters, the human and mouse versions of cone arrestin promoters are homologues. In experiments performed in mice aimed at characterizing gene expression mediated by both the mouse cone arrestin promoter (mCAR) and the human cone arrestin promoter (hCAR), strong expression was observed. However specificity was poor, with rods and RPE clearly being transduced. In experiments utilizing mCAR that were performed in dog, the same general expression pattern was seen, with strong expression observed in all classes of cones and off-target expression in rods and RPE. Table 1 summarizes results of cone targeted promoter that have been used (to date) in AAV mediated gene delivery to the retina.

It has been our experience when utilizing photoreceptor specific promoters with AAV that specificity increases when moving from rodent (mouse and rat) to dog, and that the source organism from which the promoter sequence originated has little effect. In the few cases where photoreceptor promoters have been tested in primates, the results have been consistent with those obtained in dog. Therefore, in terms of predicting promoter activity in humans, we place emphasis on results obtained in dog experiments.

Ying et al. created a transgenic mouse line in which position −151 to +126 of human cone transducin alpha-subunit (GNAT2) gene was fused to chloramphenicol acetyltransferase gene followed by position −1622 to −1409 of the interphotoreceptor retinoid-binding protein (IRBP) gene (Ying et al. (1998)). Later, Ying et al. used the same general arrangement of elements to create a transgenic mouse line in which the goal was to ablate cone photoreceptors (Ying et al. (2000)). See FIG. 1 of Ying et al. (2000) for the arrangement of elements used by Ying et al. A resulting transgenic mouse line was characterized by Fong et al. and found to lack cone photoreceptors, and in ventral retina rod photoreceptors were also absent (Fong et al. (2005)). The region-specific absence of rod photoreceptors was reported as a consequence of developmental defect due to lack of cones. However, given that only 2.5% of photoreceptors are cones, loss of rods may have been due to mis-expression of the diphtheria toxin in rods.

BRIEF SUMMARY OF THE INVENTION

The subject invention concerns materials and methods for providing for cone cell specific expression of a polynucleotide in a human or animal. One aspect of the invention concerns a polynucleotide promoter sequence that directs expression of an operably linked polynucleotide in cone cells. In one embodiment, a polynucleotide of the invention comprises an enhancer nucleotide sequence of an interphotoreceptor retinoid-binding protein (IRBP) gene that is positioned upstream (5') of a promoter nucleotide sequence of a cone transducin alpha-subunit (GNAT2) gene. In a specific embodiment, the nucleotide sequence of IRBP comprises sequence −1619 to −1411 of the IRBP gene (SEQ ID NO:2) and the nucleotide sequence of GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof. In another embodiment, a polynucleotide of the invention comprises the nucleotide sequence shown in SEQ ID NO:1, or a functional fragment and/or variant thereof.

Another aspect of the subject invention concerns methods for expressing a selected polynucleotide in cone cells. The selected polynucleotide can be provided in a polynucleotide of the invention wherein the selected polynucleotide is operably linked to a polynucleotide promoter sequence of the invention. In one embodiment, the selected polynucleotide sequence is provided in a polynucleotide vector of the invention. The vector comprising the selected polynucleotide is then introduced into a cell. The selected polynucleotide is expressed only in cone cells, with very little, if any, expression in rods or other cells. A selected polynucleotide can be one that encodes, for example, a therapeutic protein or a functional protein that is defective or underexpressed in the targeted cone cells.

BRIEF DESCRIPTION OF THE DRAWINGS

FIG. 2A shows a section of mouse retina treated with AAV5-IRBP/GNAT2-GFP at 20× magnification. FIG. 2B shows a section of mouse retina treated with AAV5-IRBP/GNAT2-GFP at 40× magnification.

FIG. 4A shows fundus analysis 4 weeks post subretinal infection of AAV5-IRBP-GNAT2-hGFP in the NRL −/− (all cone) mice. FIG. 4B shows retinal section from eye 2 immunostained for GFP at 20× magnification.

FIG. 5A shows a section of dog retina treated with AAV5-IRBP/GNAT2-hGFP immunostained for L/M opsin and GFP at 40× magnification.

FIG. 5B shows a section of dog retina treated with AAV5-IRBP/GNAT2-hGFP immunostained for S opsin and GFP at 40× magnification.

FIG. 10A: GFP expression in photoreceptors of C57 BL/6J at 2 months of post-injected retina. FIG. 10B: PNA staining of all the cone cells in 2 months post-injected C57 BL/6J transverse retina section that expressing GFP. Blue: DAPI. FIG. 10C: PNA staining of cone cells in retinal section from injected C57 BL/6J mice RPE, retinal pigment epithelium; OS, outer segment; IS, inner segment; ONL, outer nuclear layer; OPL, outer plexiform layer. Bars=50 μm.

FIGS. 11A-1-11A-3, 11B-1-11B-3. Comparison of targeted GFP gene expression in M- and S-cones. FIGS. 11A-1-11A-3: GFP expression driven by IRBP/GNAT2 promoter in M- and S-cones. FIG. 11A-1: GFP gene expression directed by IRBP/GNAT2 promoter; FIG. 11A-2: cone cells immunolabeled by M- and S-cone opsin; FIG. 11A-3: S+M-opsin labeling (red) co-localizes with GFP gene expression (green) positive cells, the cell nuclei are shown in blue with DAPI; FIGS. 11B-1-11B-3: GFP expression driven by mCAR promoter in M- and S-cones. FIG. 11B-1: GFP gene expression directed by mCAR promoter, not only in cones, but also in RPE cells; FIG. 11B-2: cone cells immunolabeled by M- and S-cone opsin; FIG. 11B-3: S+M-opsin labeling (red) co-localizes with GFP gene expression (green) positive cells, the cell nuclei are shown in blue with DAPI. GFP fluorescence was clearly visualized also in RPE cells. Bars=50 μm. RPE, retinal pigment epithelium; OS, outer segment; IS, inner segment; ONL, outer nuclear layer; OPL, outer plexiform layer.

BRIEF DESCRIPTION OF THE SEQUENCES

Figure 1A:
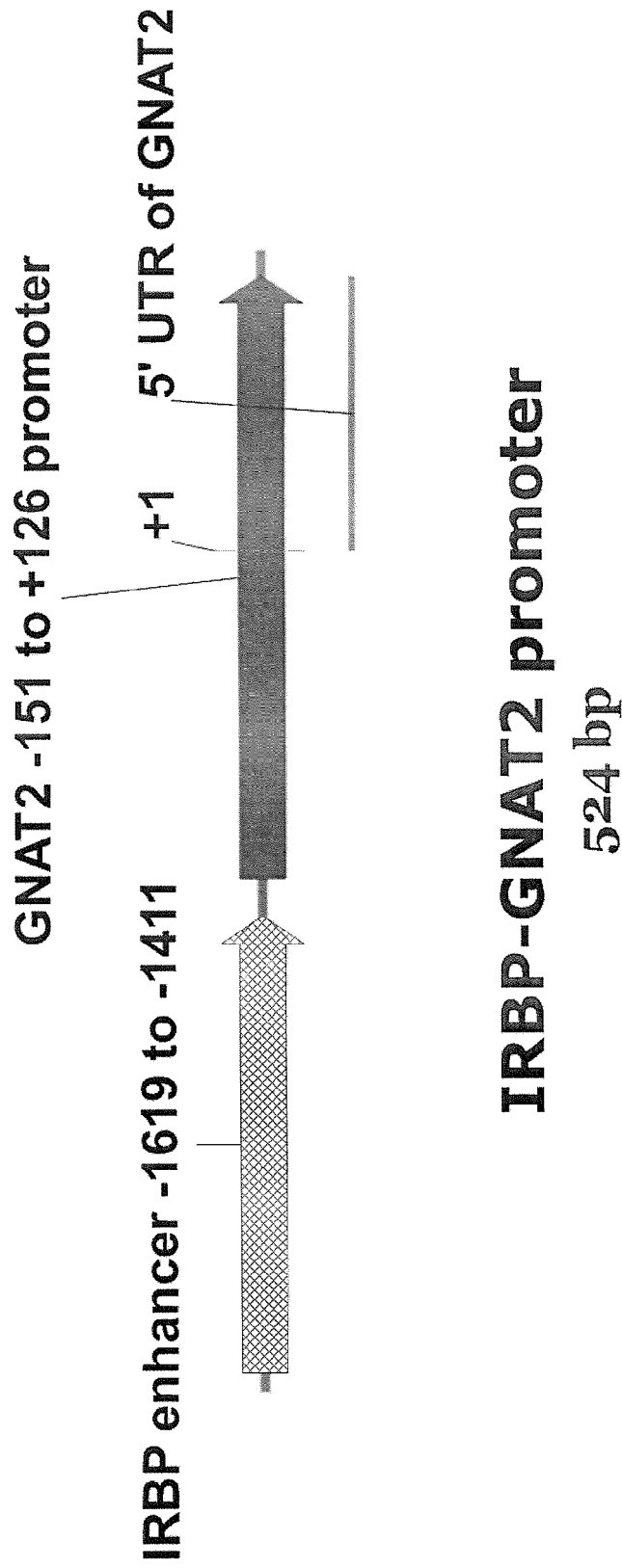
FIGS. 1A and 1B. Chimeric IRBP/GNAT2 promoter (FIG. 1A) and an AAV vector construct incorporating chimeric IRBP/GNAT2 promoter driving the reporter gene hGFP (FIG. 1B).

SEQ ID NO:1 is a chimeric IRBP/GNAT2 polynucleotide of the invention that provides for cone cell specific expression.

SEQ ID NO:2 represents nucleotides −1619 to −1411 of a human IRBP gene.

SEQ ID NO:3 represents nucleotides −151 to +126 of a human GNAT2 gene.

SEQ ID NO:4 is a chimeric IRBP/GNAT2 polynucleotide of the invention that includes 5' EcoR1 and 3'Xba1 and Xho1 restriction sites.

SEQ ID NO:5 is a human CNGB3 polypeptide.

SEQ ID NO:6 is a human CNGA3 protein.

DETAILED DESCRIPTION OF THE INVENTION

The subject invention concerns materials and methods for providing for cone cell specific expression of a polynucleotide in a human or animal. One aspect of the invention concerns a polynucleotide promoter sequence that directs expression of an operably linked polynucleotide in cone cells. In one embodiment, a polynucleotide of the invention comprises an enhancer nucleotide sequence of an interphotoreceptor retinoid-binding protein (IRBP) gene that is positioned upstream of a promoter nucleotide sequence of a cone transducin alpha-subunit (GNAT2) gene. In one embodiment, the GNAT2 gene sequence of the invention comprises the transcription start site and sequence corresponding to all or part of the 5' untranslated region (5' UTR) of GNAT2. In one embodiment, a polynucleotide of the invention comprises nucleotide sequence from about nucleotide −1650 to about −1350 of the IRBP gene sequence, or a functional fragment and/or variant thereof. In one embodiment, a polynucleotide of the invention comprises nucleotide sequence from about nucleotide −200 to about +200 of the GNAT2 gene sequence, or a functional fragment and/or variant thereof. In a further embodiment, a polynucleotide of the invention comprises the nucleotide sequence shown in SEQ ID NO:1, or a functional fragment and/or variant thereof. In a specific embodiment, the nucleotide sequence of IRBP comprises sequence −1619 to −1411 of the human IRBP gene (SEQ ID NO:2) and the nucleotide sequence of human GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof. IRBP and GNAT2 sequences can be from any mammal, such as mouse, rat, dog, etc., or any primate, including chimpanzee, or human. Polynucleotides of the invention can also comprise a nucleotide sequence encoding a therapeutic protein or a functional protein or a detectable reporter protein of interest (e.g., green fluorescent protein). In one embodiment, the polynucleotide encodes a CNG channel polypeptide. In one embodiment, the CNG channel protein is a mammalian CNG channel protein, such as a human CNG channel protein. In one embodiment, the CNG polypeptide is a CNGA3 or a CNGB3 polypeptide, or a functional fragment or variant thereof. In a specific embodiment, the CNG3B polypeptide comprises the amino acid sequence of SEQ ID NO:5, or a functional fragment or variant thereof. In one embodiment, a polynucleotide of the invention is provided in an AAV vector construct.

Another aspect of the subject invention concerns methods for expressing a selected polynucleotide in cone cells. The selected polynucleotide can be provided in a polynucleotide of the invention wherein the selected polynucleotide is operably linked to a polynucleotide promoter sequence of the invention. In one embodiment, a polynucleotide of the invention used in the method comprises an IRBP gene sequence positioned upstream of a GNAT2 gene sequence. In one embodiment, a polynucleotide of the invention used in the method comprises nucleotide sequence from about nucleotide −1650 to about −1350 of the IRBP gene sequence, or a functional fragment and/or variant thereof. In one embodiment, a polynucleotide of the invention used in the method comprises nucleotide sequence from about nucleotide −200 to about +200 of the GNAT2 gene sequence, or a functional fragment and/or variant thereof. In a further embodiment, a polynucleotide of the invention comprises the nucleotide sequence shown in SEQ ID NO:1, or a functional fragment and/or variant thereof. In a specific embodiment, the nucleotide sequence of IRBP comprises sequence −1619 to −1411 of the human IRBP gene (SEQ ID NO:2) and the nucleotide sequence of human GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof. In one embodiment, the selected polynucleotide sequence is provided in a polynucleotide vector of the invention. The vector comprising the selected polynucleotide is then introduced into a cell. In the present invention, the selected polynucleotide is expressed only in cone cells, with very little, if any, expression in rods or other cells. A selected polynucleotide can be one that encodes, for example, a therapeutic protein or a functional protein that is defective or underexpressed in the targeted cone cells. A selected polynucleotide can also encode a reporter protein that can be readily detected or identified, such as luciferase, green fluorescent protein (GFP), enhanced GFP, horseradish peroxidase, etc.

The subject invention also concerns expression constructs and vectors comprising a polynucleotide of the invention operably linked to an amino acid coding sequence and/or regulatory sequences. In one embodiment, an expression construct or vector of the invention comprises an IRBP gene sequence positioned upstream of a GNAT2 gene sequence. In one embodiment, an expression construct or vector of the invention comprises nucleotide sequence from about nucleotide −1650 to about −1350 of the IRBP gene sequence, or a functional fragment and/or variant thereof. In one embodiment, an expression construct or vector of the invention comprises nucleotide sequence from about nucleotide −200 to about +200 of the GNAT2 gene sequence, or a functional fragment and/or variant thereof. In one embodiment, an expression construct or vector of the invention comprises the nucleotide sequence shown in SEQ ID NO:1, or a functional fragment and/or variant thereof. In a specific embodiment, the nucleotide sequence of IRBP comprises sequence −1619 to −1411 of the human IRBP gene (SEQ ID NO:2) and the nucleotide sequence of human GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof. In one embodiment, the amino acid coding sequence codes for a protein whose expression in a cone cell provides for treatment of a disease or condition of a cone cell. In one embodiment, the amino acid coding sequence codes for a cone cyclic nucleotide-gated channel (CNG) protein, such as CNGB3 and CNGA3, or a functional fragment or variant thereof. In a specific embodiment, the CNGB3 protein comprises the amino acid sequence of SEQ ID NO:5, or a functional fragment or variant thereof. In one embodiment, the disease or condition is achromatopsia. In another embodiment, the disease or condition is progressive cone dystrophy.

In one embodiment, a vector construct of the present invention is an AAV vector. An AAV vector of the invention can be of any AAV serotype, including, but not limited to, serotype AAV1, AAV2, AAV3, AAV4, AAV5, AAV6, AAV7, AAV8, AAV9, AAV10, and AAV11. In a specific embodiment, an AAV5 serotype is utilized. In one embodiment, an AAV vector of the invention comprises inverted terminal repeats (ITR).

The subject invention also concerns a virus or virion comprising a polynucleotide, expression construct, or vector construct of the invention. In one embodiment, the virus or virion is an AAV virus. Methods for preparing viruses and virions comprising a heterologous polynucleotide or construct are known in the art. In the case of AAV, cells can be coinfected or transfected with adenovirus or polynucleotide constructs comprising adenovirus genes suitable for AAV helper function. Examples of materials and methods are described, for example, in U.S. Pat. Nos. 8,137,962 and 6,967,018.

The subject invention also concerns methods for treating or ameliorating diseases and/or conditions that are associated with cone photoreceptors. In one embodiment, a method of the invention comprises administering an expression construct or vector of the invention that also comprises a polynucleotide sequence that codes for a polypeptide that provides for treatment or amelioration of the disease or condition. In one embodiment, a polynucleotide of the invention used in the method comprises an IRBP gene sequence positioned upstream of a GNAT2 gene sequence. In one embodiment, a polynucleotide of the invention used in the method comprises nucleotide sequence from about nucleotide −1650 to about −1350 of the IRBP gene sequence, or a functional fragment and/or variant thereof. In one embodiment, a polynucleotide of the invention used in the method comprises nucleotide sequence from about nucleotide −200 to about +200 of the GNAT2 gene sequence, or a functional fragment and/or variant thereof. In one embodiment, a polynucleotide of the invention comprises the nucleotide sequence shown in SEQ ID NO:1, or a functional fragment and/or variant thereof. In a specific embodiment, the nucleotide sequence of IRBP comprises sequence −1619 to −1411 of the IRBP gene (SEQ ID NO:2) and the nucleotide sequence of GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof. In one embodiment, a construct or vector of the invention is administered by parenteral administration, such as intravenous, intramuscular, intraocular, intranasal, etc. The construct or vector can be administered in vivo or ex vivo.

In one embodiment, the disease or condition to be treated is achromatopsia. In a further embodiment, the disease or condition to be treated is progressive cone dystrophy. In one embodiment, a polypeptide encoded by the expression construct or vector to be administered is a cone cyclic nucleotide-gated ion channel polypeptide (CNG). In one embodiment, the polypeptide is a CNGA3 polypeptide (see, e.g., GenBank Accession Nos: AAH96300.1, Q16281.2, and AAH96298.1). In another embodiment, the polypeptide is a CNG3B polypeptide (see, e.g., GenBank Accession Nos. AAF86274.1, NP 061971.3, and NM 019098.4). In a further embodiment, a polypeptide encoded by the expression construct or vector is a guanine nucleotide binding protein α-transducing activity polypeptide 2 (GNAT2). In one embodiment, the encoded polypeptide is a mammalian polypeptide. In a further embodiment, the polypeptide is a human polypeptide. In a specific embodiment, a human CNGB3 polypeptide comprises the sequence shown in SEQ ID NO:5. In a specific embodiment, a human CNGA3 protein comprises the sequence shown in SEQ ID NO:6. In a further embodiment, the encoded polypeptide is an opsin, e.g., M-opsin or L-opsin. Dosage regimes and effective amounts to be administered can be determined by ordinarily skilled clinicians. Administration may be in the form of a single dose or multiple doses. Standard methods for performing gene therapy using polynucleotides, expression constructs, and vectors are known in the art (see, for example, Gene Therapy: Principles and Applications, Springer Verlag 1999; and U.S. Pat. Nos. 6,461,606; 6,204,251 and 6,106,826).

The subject invention also concerns a cell comprising a polynucleotide of the invention. In one embodiment, the cell is a cone cell. In another embodiment, the cell is a human cell. In a specific embodiment, the cell is a human cone cell. The cell can express a nucleotide sequence operably linked to a polynucleotide of the invention. In one embodiment, a polynucleotide of the invention is provided in an expression construct and/or vector. In one embodiment, an expression construct or vector of the invention comprises an IRBP gene sequence positioned upstream of a GNAT2 gene sequence. In one embodiment, a polynucleotide of the invention comprises nucleotide sequence from about nucleotide −1650 to about −1350 of the IRBP gene sequence, or a functional fragment and/or variant thereof. In one embodiment, a polynucleotide of the invention comprises nucleotide sequence from about nucleotide −200 to about +200 of the GNAT2 gene sequence, or a functional fragment and/or variant thereof. In one embodiment, a polynucleotide of the invention comprises the nucleotide sequence shown in SEQ ID NO:1, or a functional fragment and/or variant thereof. In a specific embodiment, the nucleotide sequence of IRBP comprises sequence −1619 to −1411 of the human IRBP gene (SEQ ID NO:2) and the nucleotide sequence of human GNAT2 comprises sequence −151 to +126 of the GNAT2 gene (SEQ ID NO:3). In one embodiment, there is no intervening sequence between the IRBP and GNAT2 sequences of the polynucleotide. In an exemplified embodiment, a polynucleotide of the invention comprises the nucleotide sequence shown in SEQ ID NO:4, or a functional fragment and/or variant thereof.

Polynucleotide expression constructs of the invention comprise one or more copies of a polynucleotide of the present invention that directs expression of an operably linked nucleotide sequence in cone cells. As used herein, the term "expression construct" refers to a combination of nucleic acid sequences that provides for transcription of an operably linked nucleic acid sequence. As used herein, the term "operably linked" refers to a juxtaposition of the components described wherein the components are in a relationship that permits them to function in their intended manner. In general, operably linked components are in contiguous relation.

Expression constructs of the invention will also generally include regulatory elements that are functional in the intended host cell in which the expression construct is to be expressed. Thus, a person of ordinary skill in the art can select regulatory elements for use in, for example, bacterial host cells, yeast host cells, plant host cells, insect host cells, mammalian host cells, and human host cells. Regulatory elements include promoters, transcription termination sequences, translation termination sequences, enhancers, and polyadenylation elements.

An expression construct of the invention can comprise a polynucleotide promoter sequence of the invention operably linked to a nucleotide sequence encoding a desired polypeptide. Polynucleotide promoters of the invention can be incorporated into an expression construct using standard techniques known in the art. Single or multiple copies of promoters or multiple promoters of the invention can be used in an expression construct of the invention.

Expression constructs of the invention may optionally contain a transcription termination sequence, a translation termination sequence, signal peptide sequence, internal ribosome entry sites (IRES), and/or enhancer elements. Transcription termination regions can typically be obtained from the 3' untranslated region of a eukaryotic or viral gene sequence. Transcription termination sequences can be positioned downstream of a coding sequence to provide for efficient termination. Signal peptides are a group of short amino terminal sequences that encode information responsible for the relocation of an operably linked peptide to a wide range of post-translational cellular destinations, ranging from a specific organelle compartment to sites of protein action and the extracellular environment. Enhancers are cis-acting elements that increase gene transcription and can also be included in the expression construct. Enhancer elements are known in the art, and include, but are not limited to, the CaMV 35S enhancer element, cytomegalovirus (CMV) early promoter enhancer element, and the SV40 enhancer element. DNA sequences which direct polyadenylation of the mRNA encoded by the structural gene can also be included in the expression construct.

Unique restriction enzyme sites can be included at the 5' and 3' ends of the expression construct to allow for insertion into a polynucleotide vector. As used herein, the term "vector" refers to any genetic element, including for example, plasmids, cosmids, chromosomes, phage, virus, and the like, which is capable of replication when associated with proper control elements and which can transfer polynucleotide sequences between cells. Vectors contain a nucleotide sequence that permits the vector to replicate in a selected host cell. A number of vectors are available for expression and/or cloning, and include, but are not limited to, pBR322, pUC series, M13 series, and pBLUESCRIPT vectors (Stratagene, La Jolla, Calif.). Viral vectors include, but are not limited to, retroviral vectors, lentiviral vectors, adenoviral vectors, adeno-associated viral (AAV) vectors, herpes viral vectors, etc. (see, for example, U.S. Pat. Nos. 7,094,604; 6,660,514; 6,165,781).

Polynucleotides, expression constructs, and vectors of the subject invention can be introduced into a cell by methods known in the art. Such methods include transfection, microinjection, electroporation, lipofection, cell fusion, calcium phosphate precipitation, and by biolistic methods. In one embodiment, a polynucleotide or expression construct of the invention can be introduced in vivo via a viral vector such as adeno-associated virus (AAV), herpes simplex virus (HSV), papillomavirus, adenovirus, and Epstein-Barr-virus (EBV). Attenuated or defective forms of viral vectors that can be used with the subject invention are known in the art. Typically, defective virus is not capable of infection after the virus is introduced into a cell. Polynucleotides, vectors, and expression constructs of the invention can also be introduced in vivo via lipofection (DNA transfection via liposomes prepared from synthetic cationic lipids) (Feigner et al., 1987). Synthetic cationic lipids (LIPOFECTIN, Invitrogen Corp., La Jolla, Calif.) can be used to prepare liposomes to encapsulate a polynucleotide, vector, or expression construct of the invention. A polynucleotide, vector, or expression construct of the invention can also be introduced in vivo as naked DNA using methods known in the art, such as transfection, microinjection, electroporation, calcium phosphate precipitation, and by biolistic methods.

Polynucleotides of the subject invention can also be defined in terms of more particular identity and/or similarity ranges with those exemplified herein. The sequence identity will typically be greater than 60%, preferably greater than 75%, more preferably greater than 80%, even more preferably greater than 90%, and can be greater than 95%. The identity and/or similarity of a sequence can be 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99% or greater as compared to a sequence exemplified herein. Unless otherwise specified, as used herein percent sequence identity and/or similarity of two sequences can be determined using the algorithm of Karlin and Altschul (1990), modified as in Karlin and Altschul (1993). Such an algorithm is incorporated into the NBLAST and XBLAST programs of Altschul et al. (1990). BLAST searches can be performed with the NBLAST program, score=100, wordlength=12, to obtain sequences with the desired percent sequence identity. To obtain gapped alignments for comparison purposes, Gapped BLAST can be used as described in Altschul et al. (1997). When utilizing BLAST and Gapped BLAST programs, the default parameters of the respective programs (NBLAST and XBLAST) can be used. See NCBI/NIH website.

The subject invention also contemplates those polynucleotide molecules having sequences which are sufficiently homologous with the polynucleotide sequences of the invention so as to permit hybridization with that sequence under standard stringent conditions and standard methods (Maniatis, T. et al., 1982). As used herein, "stringent" conditions for hybridization refers to conditions wherein hybridization is typically carried out overnight at 20-25 C below the melting temperature (Tm) of the DNA hybrid in 6×SSPE, 5× Denhardt's solution, 0.1% SDS, 0.1 mg/ml denatured DNA. The melting temperature is described by the following formula (Beltz, G. A. et al., 1983):

$$Tm = 81.5\ C + 16.6\ \text{Log}\ [Na+] + 0.41\ (\%\ G+C) - 0.61\ (\%\ \text{formamide}) - 600/\text{length of duplex in base pairs}.$$

Washes are typically carried out as follows:

(1) Twice at room temperature for 15 minutes in 1×SSPE, 0.1% SDS (low stringency wash).

(2) Once at Tm−20 C for 15 minutes in 0.2×SSPE, 0.1% SDS (moderate stringency wash).

As used herein, the terms "nucleic acid" and "polynucleotide sequence" refer to a deoxyribonucleotide or ribonucleotide polymer in either single- or double-stranded form, and unless otherwise limited, would encompass known analogs of natural nucleotides that can function in a similar manner as naturally-occurring nucleotides. The polynucleotide sequences include both full-length sequences as well as shorter sequences derived from the full-length sequences. It is understood that a particular polynucleotide sequence includes the degenerate codons of the native sequence or sequences which may be introduced to provide codon preference in a specific host cell. The polynucleotide sequences falling within the scope of the subject invention further include sequences which specifically hybridize with the sequences coding for a peptide of the invention. The polynucleotide includes both the sense and antisense strands as either individual strands or in the duplex.

Fragments and variants of a polynucleotide or polypeptide of the present invention can be generated as described herein and tested for the presence of function using standard techniques known in the art. Thus, an ordinarily skilled artisan can readily prepare and test fragments and variants of a polynucleotide or polypeptide of the invention and determine whether the fragment or variant retains functional activity that is the same or similar to a full-length or a non-variant polynucleotide or polypeptide, such as cone-specific promoter activity, or formation of ion channels in response to cyclic nucleotides.

As those skilled in the art can readily appreciate, there can be a number of variant sequences of a protein found in nature, in addition to those variants that can be artificially created by the skilled artisan in the lab. The polynucleotides and polypeptides of the subject invention encompasses those specifically exemplified herein, as well as any natural variants thereof, as well as any variants which can be created artificially, so long as those variants retain the desired functional activity.

Also within the scope of the subject invention are polypeptides which have the same amino acid sequences of a polypeptide exemplified herein except for amino acid substitutions, additions, or deletions within the sequence of the polypeptide, as long as these variant polypeptides retain substantially the same relevant functional activity as the polypeptides specifically exemplified herein. For example, conservative amino acid substitutions within a polypeptide which do not affect the function of the polypeptide would be within the scope of the subject invention. Thus, the polypeptides disclosed herein should be understood to include variants and fragments, as discussed above, of the specifically exemplified sequences.

The subject invention further includes nucleotide sequences which encode the polypeptides disclosed herein. These nucleotide sequences can be readily constructed by those skilled in the art having the knowledge of the protein and amino acid sequences which are presented herein. As would be appreciated by one skilled in the art, the degeneracy of the genetic code enables the artisan to construct a variety of nucleotide sequences that encode a particular polypeptide or protein. The choice of a particular nucleotide sequence could depend, for example, upon the codon usage of a particular expression system or host cell.

Polypeptides having substitution of amino acids other than those specifically exemplified in the subject polypeptides are also contemplated within the scope of the present invention. For example, non-natural amino acids can be substituted for the amino acids of a polypeptide of the invention, so long as the polypeptide having substituted amino acids retains substantially the same activity as the polypeptide in which amino acids have not been substituted. Examples of non-natural amino acids include, but are not limited to, ornithine, citrulline, hydroxyproline, homoserine, phenylglycine, taurine, iodotyrosine, 2,4-diaminobutyric acid, α-amino isobutyric acid, 4-aminobutyric acid, 2-amino butyric acid, γ-amino butyric acid, ∈-amino hexanoic acid, 6-amino hexanoic acid, 2-amino isobutyric acid, 3-amino propionic acid, norleucine, norvaline, sarcosine, homocitrulline, cysteic acid, τ-butylglycine, τ-butylalanine, phenylglycine, cyclohexylalanine, β-alanine, fluoro-amino acids, designer amino acids such as β-methyl amino acids, C-methyl amino acids, N-methyl amino acids, and amino acid analogues in general. Non-natural amino acids also include amino acids having derivatized side groups. Furthermore, any of the amino acids in the protein can be of the D (dextrorotary) form or L (levorotary) form.

Amino acids can be generally categorized in the following classes: non-polar, uncharged polar, basic, and acidic. Conservative substitutions whereby a polypeptide having an amino acid of one class is replaced with another amino acid of the same class fall within the scope of the subject invention so long as the polypeptide having the substitution still retains substantially the same biological activity as a polypeptide that does not have the substitution. Table 3 provides a listing of examples of amino acids belonging to each class.

The methods of the present invention can be used with humans and other animals. The other animals contemplated within the scope of the invention include domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses.

The polynucleotides contemplated within the scope of the subject invention include the specific polynucleotides exemplified herein as well as equivalent polynucleotides which may be, for example, somewhat longer or shorter than the polynucleotides exemplified herein. For example, using the teachings provided herein, a person skilled in the art could readily make polynucleotides having from 1 to about 5, 10, 15, 20, 25, 30, 35, 40, 50, 60, 70, 80, 90, 100, 110, 120, 130, 140, 150 or more nucleotides added to, or removed from, either or both ends of the disclosed polynucleotides using standard techniques known in the art. In one embodiment, nucleotides are removed from the 5' or 3' end of the invention. In a specific embodiment, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, or more nucleotides can, independently, be removed from either or both ends of a polynucleotide of the invention, or from either or both ends of an IRBP and/or GNAT2 sequence of a chimeric IRBP/GNAT2 polynucleotide of the invention. In one embodiment, any added nucleotides would be the same as the corresponding nucleotides of the IBRP or GNAT2 gene sequences. Added nucleotide sequences can also provide for restriction sites recognized by one or more restriction endonucleases. The skilled artisan, having the benefit of the teachings disclosed in the subject application, could easily determine whether a variant polynucleotide retained the functional activity of the specific polynucleotides exemplified herein. Such a longer or shorter polynucleotide would be within the scope of the subject invention as long as said polynucleotide retains substantially the same relevant functional activity as the polynucleotides exemplified herein. For example, a longer or shorter variant of an exemplified polynucleotide (e.g., SEQ ID NO:1, SEQ ID NO:2, SEQUENCE ID NO:3, or SEQ ID NO:4) would fall within the scope of the subject invention if the longer or shorter variant polynucleotide had the ability to promote expression in cone cells. In another example, nucleotides can be added or removed between the IRBP and GNAT2 sequences of a chimeric IRBP/GNAT2 polynucleotide of the invention. Similarly, nucleotides can be added or removed from the IRBP and/or GNAT2 sequences of a chimeric IRBP/GNAT2 polynucleotide of the invention as long as the polynucleotide retains substantially the same functional activity, i.e., promotes expression in cone cells, as an exemplified polynucleotide. Methods of identifying whether a fragment of a polynucleotide promoter is capable of initiating gene transcription are well known in the art. U.S. Pat. Nos. 6,080,914 and 5,986,174 provide assay systems that can be used for analysis of promoter fragments for activity.

Also within the scope of the subject invention are polynucleotides which have the same nucleotide sequences of a polynucleotide exemplified herein except for nucleotide substitutions, additions, or deletions within the sequence of the polynucleotide, as long as these variant polynucleotides retain substantially the same relevant functional activity as the polynucleotides specifically exemplified herein. Thus, the polynucleotides disclosed herein should be understood to include variants and fragments, as discussed above, of the specifically exemplified sequences.

The subject invention concerns a chimeric promoter for use with viral vectors such as adeno-associated virus (AAV) for the efficient and selective targeting of transgene expression to cone photoreceptors. Constructs of the invention have direct utility as a vehicle for the delivery of therapeutic genes to diseases that affect cone photoreceptors, such as achromatopsia.

A summary of the transduction results of AAV mediated transgene expression utilizing the chimeric IRBP/GNAT2 promoter is given in Table 2.

Following are examples that illustrate procedures for practicing the invention. These examples should not be construed as limiting. All percentages are by weight and all solvent mixture proportions are by volume unless otherwise noted.

EXAMPLE 1

Description of Chimeric IRBP/GNAT2 Promoter

Figure 1B:
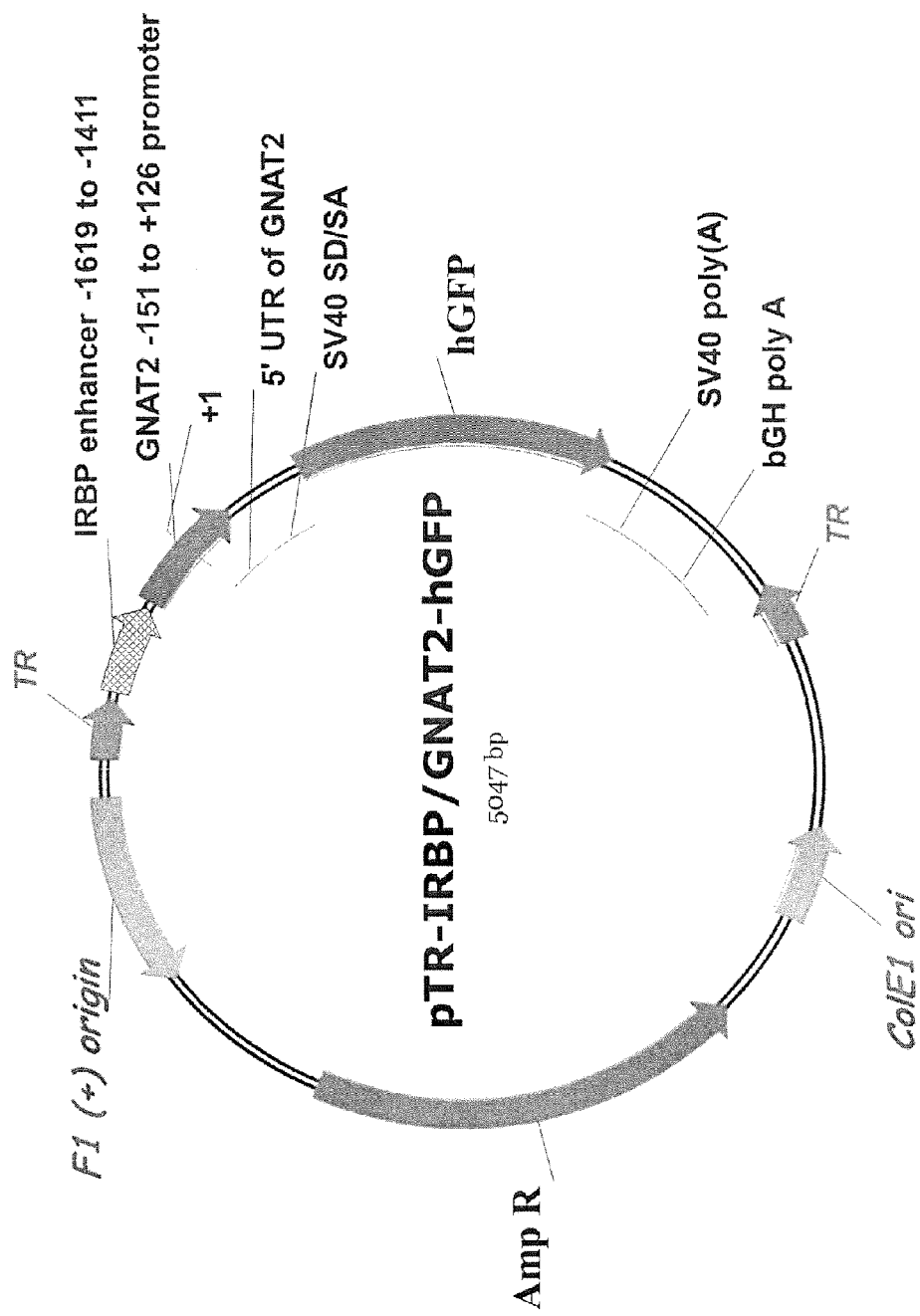

In an attempt to improve upon previous cone targeting promoters used in conjunction with AAV mediated gene delivery, we created a chimeric promoter in which the sequence corresponding to −1619 to −1411 of the interphotoreceptor retinoid-binding protein (IRBP) gene was directly fused to −151 to +126 sequence of human cone transducin alpha-subunit (GNAT2). A depiction of the chimeric IRBP/GNAT2 promoter is given in FIG. 1A. Note that the arrangement of elements differs from those used in Ying et al. (1998) and Ying et al. (2000) (see FIG. 1 of Ying et al. (2000)). In this case the IRBP element is located upstream of the GNAT2 and there is no intervening sequence between the elements.

Figure 2A:
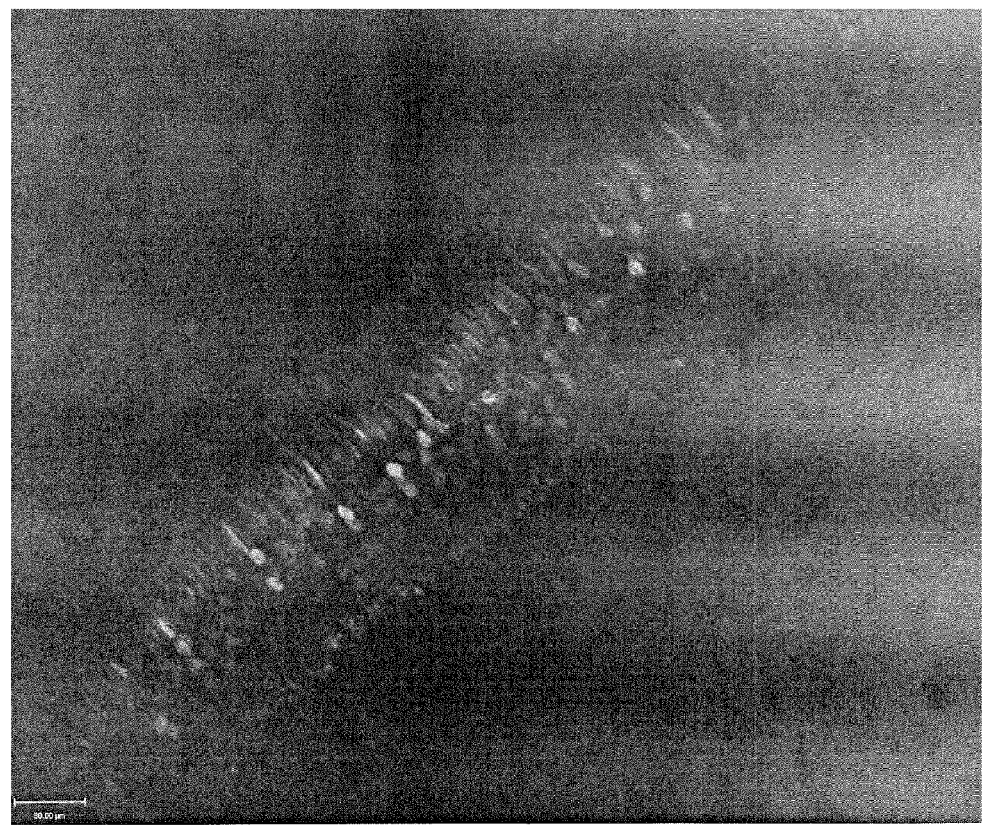
FIGS. 2A and 2B.
Figure 2B:
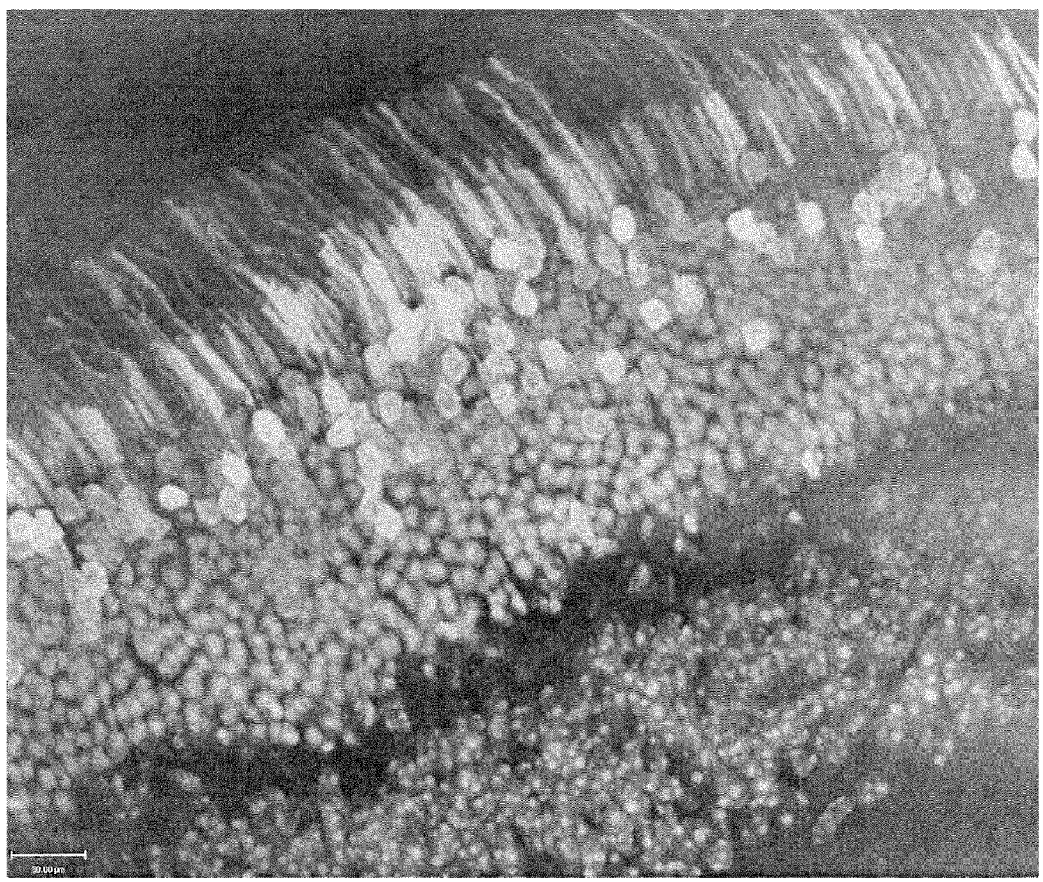

Results: The chimeric IRBP/GNAT2 promoter was incorporated into an AAV vector plasmid containing the reporter gene humanized green fluorescent protein (hGFP) (FIG. 1B) and packaged in AAV serotype 5 (AAV5). The resulting vector, AAV5-IRBP/GNAT2-GFP was tested for cone specificity in mouse retina via subretinal injection. The results depicted in FIGS. 2A and 2B, a retinal section immunostained for GFP and stained with DAPI (stain for cell nuclei, appears as blue), indicate that expression was limited to photoreceptors with no RPE expression observed. All cone photoreceptors appear to be efficiently transduced, with some expression seen in rod photoreceptors.

EXAMPLE 2

Figure 3:
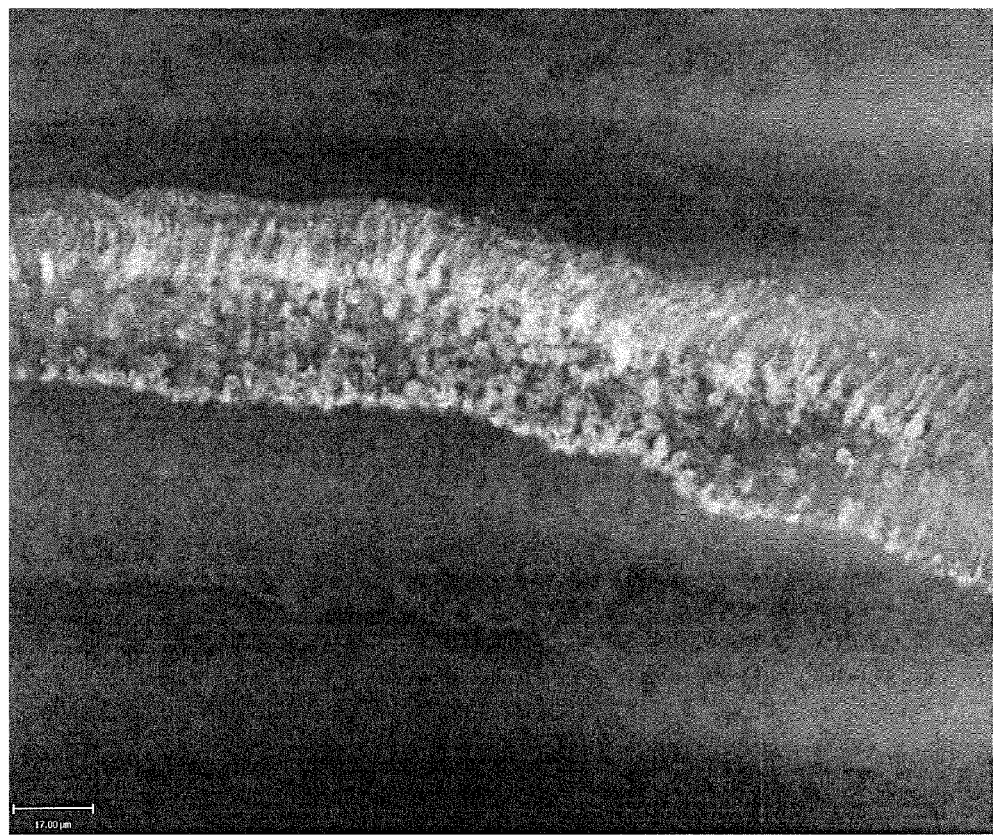
FIG. 3 shows a section of mouse retina treated with AAV5-IRBP/GNAT2-GFP+AAV5-PR2.1-mCherry at 20× magnification.

Expression mediated by the chimeric IRBP/GNAT2 promoter was directly compared to that mediated by the PR2.1 promoter. AAV5-IRBP/GNAT2-hGFP vector was mixed at an equal ratio with AAV5-PR2.1-mCherry. FIG. 3 is a retinal section from mouse that was treated with the AAV5-IRPB/GNAT2-hGFP+AAV5-PR2.1-mCherry vector mixture and immunostained for GFP and then merged with an image captured for the red channel (mCherry expression is apparent as raw red spectrum fluorescence). All cones cell bodies positive for mCherry also appear to be positive for hGFP expression as indicated by the orange color (overlay of red and green appears as orange). Many cone cell bodies are GFP positive and do not appear to be mCherry positive.

EXAMPLE 3

Figure 4A:
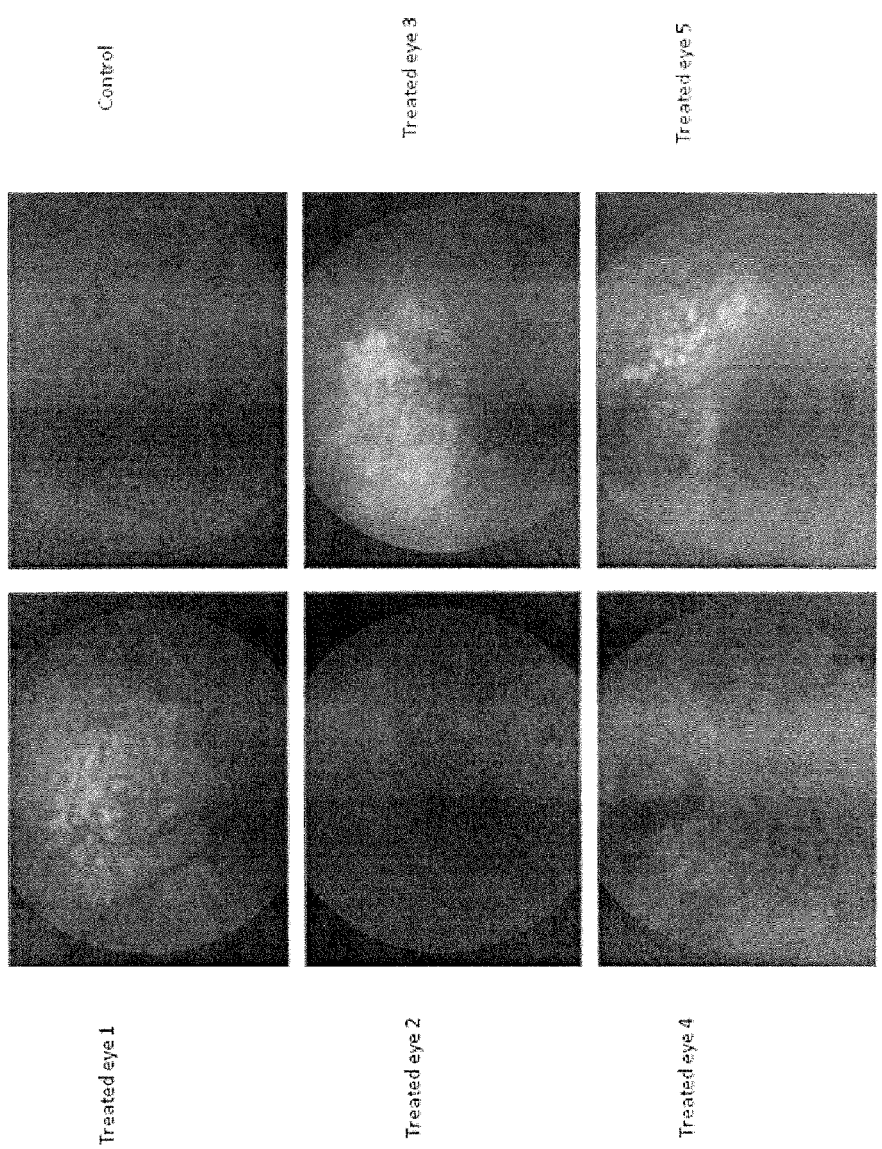
FIGS. 4A and 4B.
Figure 4B:
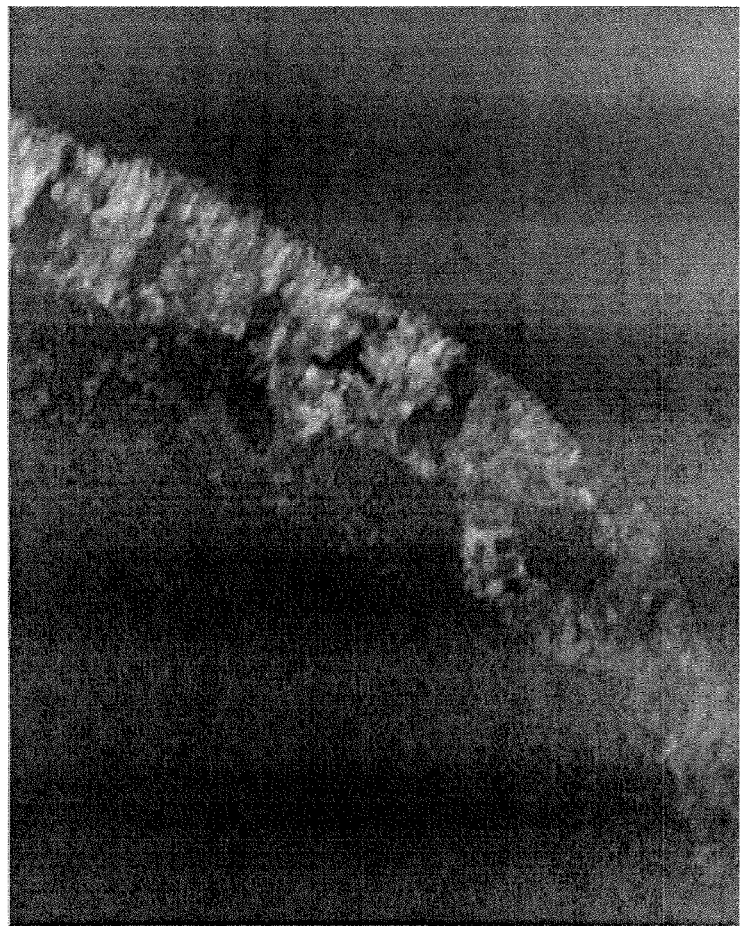

The transcription factor neural retina-specific leucine zipper protein (NRL) is required for the development of rod from photoreceptor progenitor cells (Mears et al. (2001)). Mice lacking Nrl, i.e., Nrl knock-out mice (Nrl$^{-/-}$), develop retina with an 'all cone' phenotype (Daniele et al. (2005)). Furthermore, the photoreceptor-cones of the Nrl$^{-/-}$ mouse most resemble S-cones, with levels of S-cone opsin expression and spectral sensitivity consistent with being characterized as S-cones (Nikonov et al. (2005)). In order to evaluate the ability of the chimeric IRBP-GNAT2 promoter to drive gene expression in S-cones we subretinally injected 6 week old Nrl$^{-/-}$ mice with AAV5-IRBP/GNAT2. Four weeks post injection with vector, fundus images were recorded using the appropriate filters to visualize raw GFP fluorescence (FIG. 4A). Strong GFP expression was observed in all eyes treated. Subsequently, eyes were harvested and retinas sectioned and immunostained for GFP and DAPI (FIG. 4B). GFP Expression was strong and was restricted to photoreceptor layer.

EXAMPLE 4

Figure 5A:
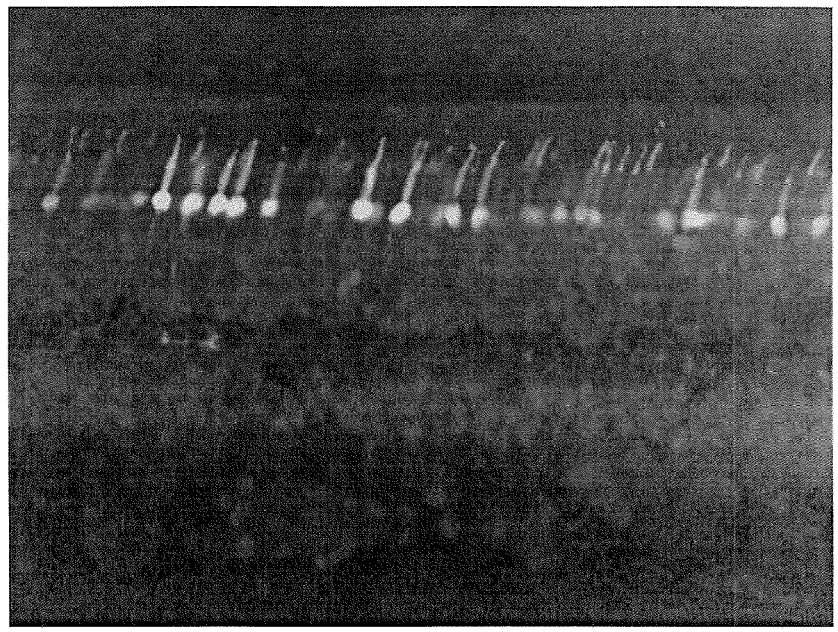
FIGS. 5A and 5B.
Figure 5B:
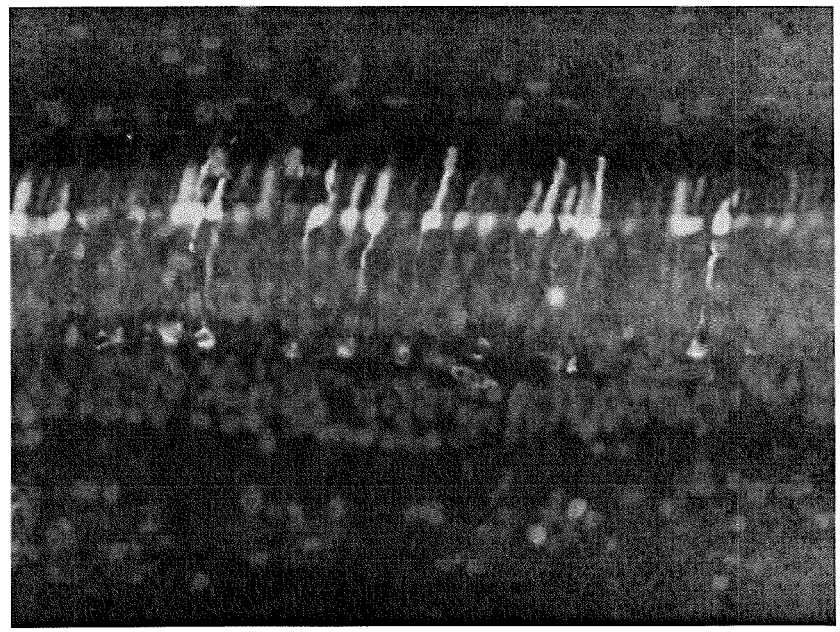

To further characterize the expression pattern of the chimeric IRBP/GNAT2 promoter, AAV5-IRBP/GNAT2-hGFP vector was subretinally injected into dog retina. FIG. 5A depicts a section of treated retina that was immunostained for L/M opsin (red) and for GFP (green). The L/M opsin staining is used to identify L/M cones. Results show that GFP signal is limited to cone cells only (as indicated by distinctive morphology of the cone cells). The majority, if not all of the L/M cones are positive for GFP expression. A different section from the same treated dog retina was immunostained with S opsin (red) and GFP (green). In this instance S opsin immunostaining is used to identify S cones (see FIG. 5B). S cones are naturally less numerous than L/M cones in dog retina, which is apparent from this image. A majority of S cones in this section are clearly positive for GFP expression.

EXAMPLE 5

Figure 6B:
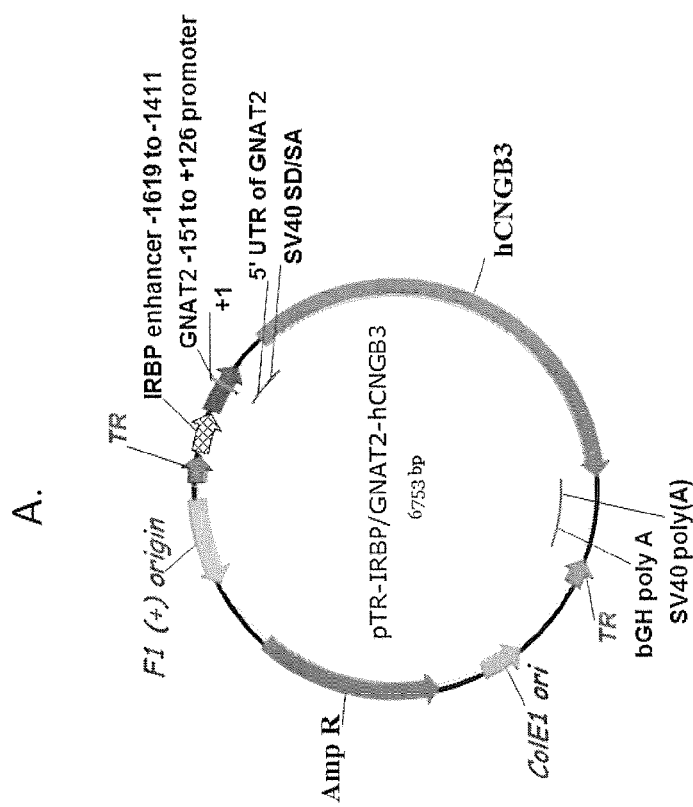
FIGS. 6A and 6B. AAV5-IRBP/GNAT2-hCNGB3 gene therapy in CNGB3 KO mouse.
Figure 6A:
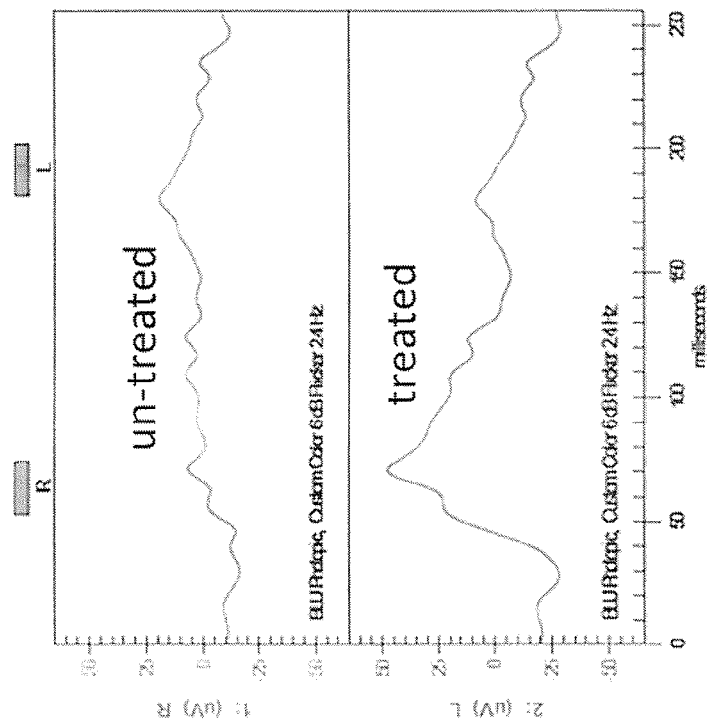

In order to evaluate the ability of the chimeric IRBP/GNAT2 promoter to drive gene expression sufficient to provide therapeutic rescue, an AAV vector construct containing the human gene for CNGB3 under the control of the IRBP/GNAT2 promoter (see FIG. 6A) was created and packaged in AAV5. The AAV5-IRBP/GNAT2-hCNGB3 vector was then subretinally injected into the left eye only of CNGB3 Knockout (CNGB3 KO) mice at 1 month of age. Six weeks later therapeutic efficacy was evaluated by cone specific electroretinogram (ERG). Untreated CNGB3 KO mice exhibit little to no cone ERG as can be seen in the upper panel of FIG. 6B. Treatment with AAV5-IRBP/GNAT2-hCNGB3 resulted in robust improvement in the amplitude of the cone ERG (FIG. 6B, lower panel).

EXAMPLE 6

Mutations in the gene encoding the beta-subunit of the cone cyclic nucleotide-gated channel (CNGB3) cause cone function loss in mammals including humans. We tested two AAV5-hCngb3 vectors with different cone targeting promoters to see if gene replacement therapy would result in restoration of cone function in the Cngb3 knockout mice, a model of human Achromatopsia 1 (ACHM1).

Methods: Human Cngb3 cDNA in conjunction with cone-targeting promoter mCAR-pro or IRBP/GNAT2 was packaged into AAV serotype 5 (AAV5-mCARpro-hCngb3 or AAV5-IRBP/GNAT2-hCngb3 at $10^{13}$ viral genome-containing particles/ml). At postnatal day 14, 1 μl of either vector was injected subretinally into one eye of groups of 20 Cngb3 knockout mice, respectively. The untreated, contralateral eyes served as controls. Dark- and light-adapted ERGs were recorded periodically from 3 weeks to 6 months after treatment. 6 months after injection, both treated and control eyes were harvested for histochemical studies.

Figures 7A, 7B, 7C:
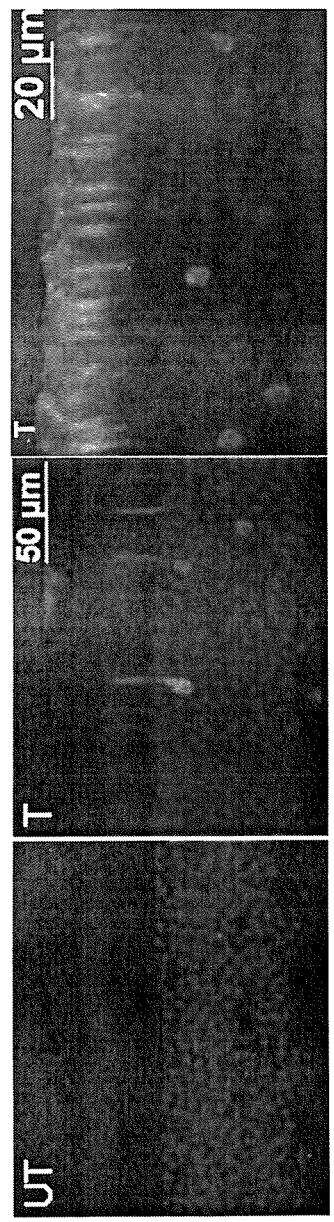
FIGS. 7A-7C. Immunohistochemistry showed human CNGB3 staining (green) in the outer segments of many cones (red: cone-specific PNA staining) in AAV5-IRBP/GNAT2-hCNGB3 treated eyes but not in cones from partner untreated eyes of Cngb3 KO mice.
Figures 8A, 8B:
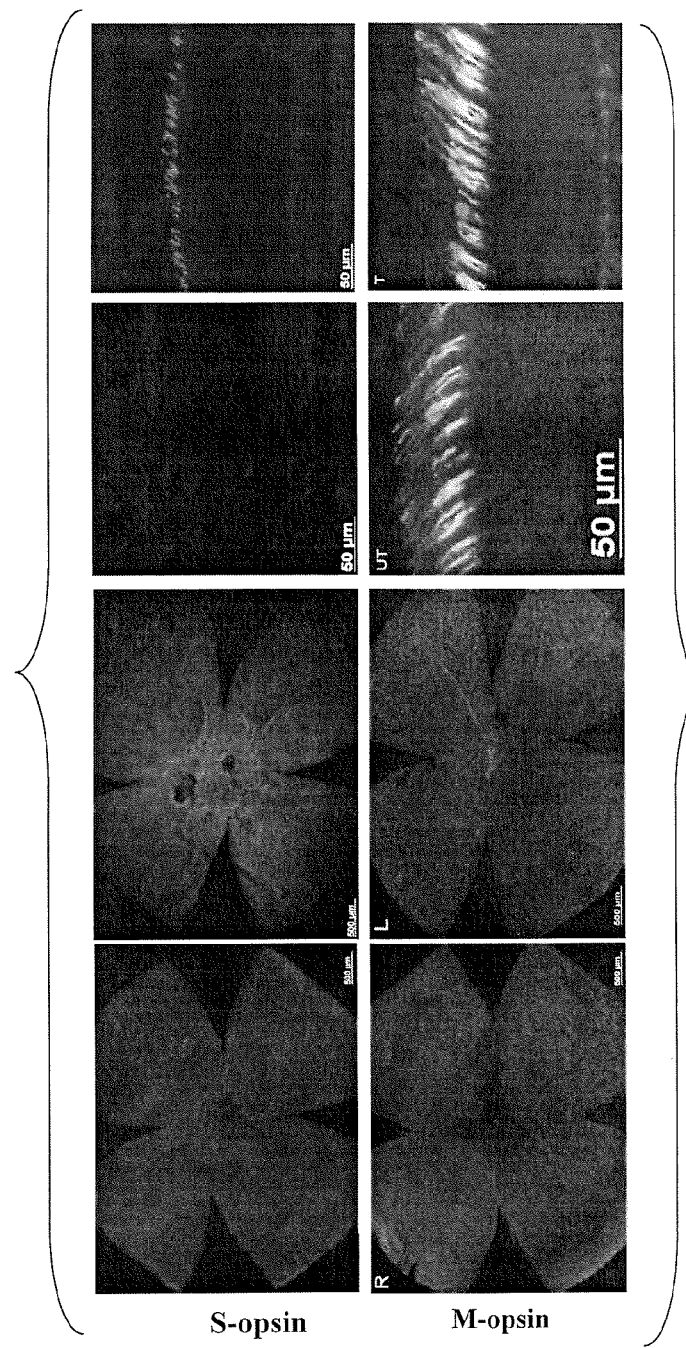
FIGS. 8A and 8B. Anti-M- (FIG. 8B) or S-opsin (FIG. 8A) staining showed that S-cones were preserved in P14+6-month AAV5-IRBP/GNAT2-hCNGB3 treated eyes but not in contralateral untreated eyes of Cngb3 KO mice. Most M-opsin containing cones remain at 6.5 months untreated Cngb3 KO mice.
Figure 9A:
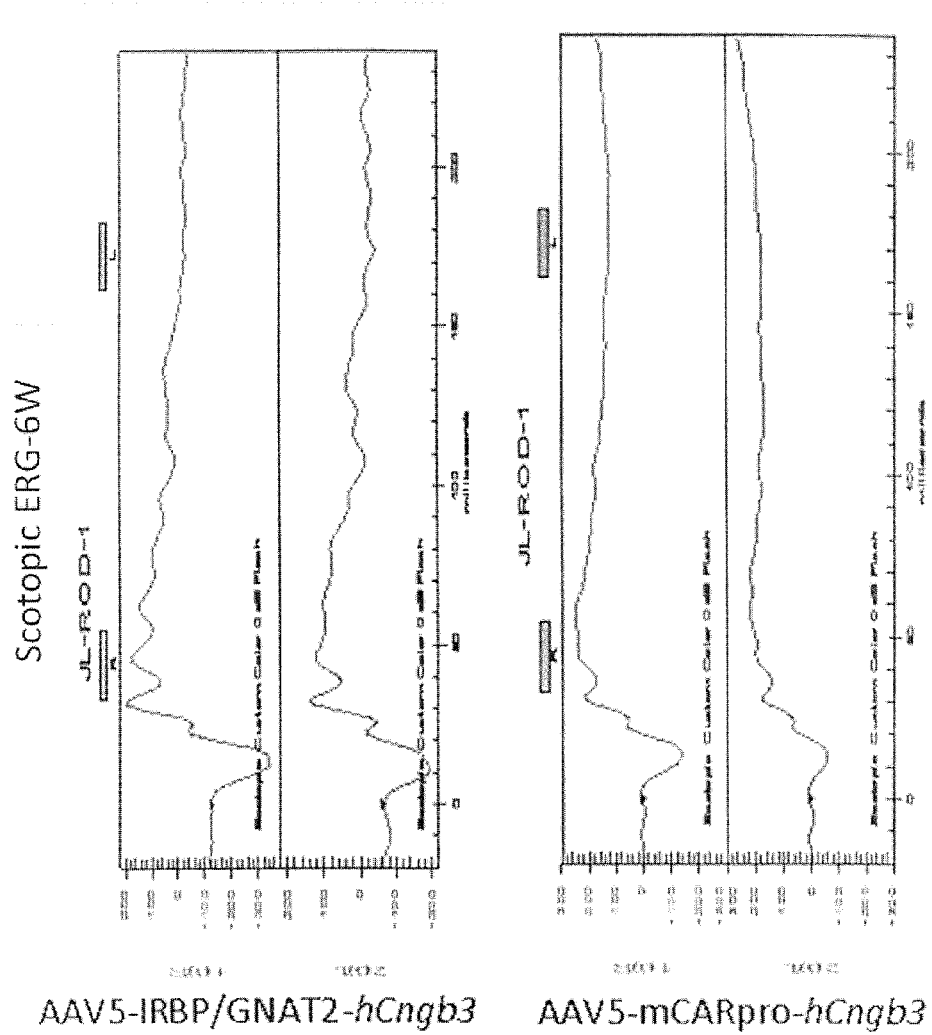
FIGS. 9A-9D. Representative ERGs from Cngb3 KO mice either treated with AAV5-IRBP/GNAT2-hCNGB3 or AAV5-mCAR-pro-hCNGB3 at 6-week or 6-month following treatment at P14. Only left eyes were treated in each mouse.
Figure 9B:
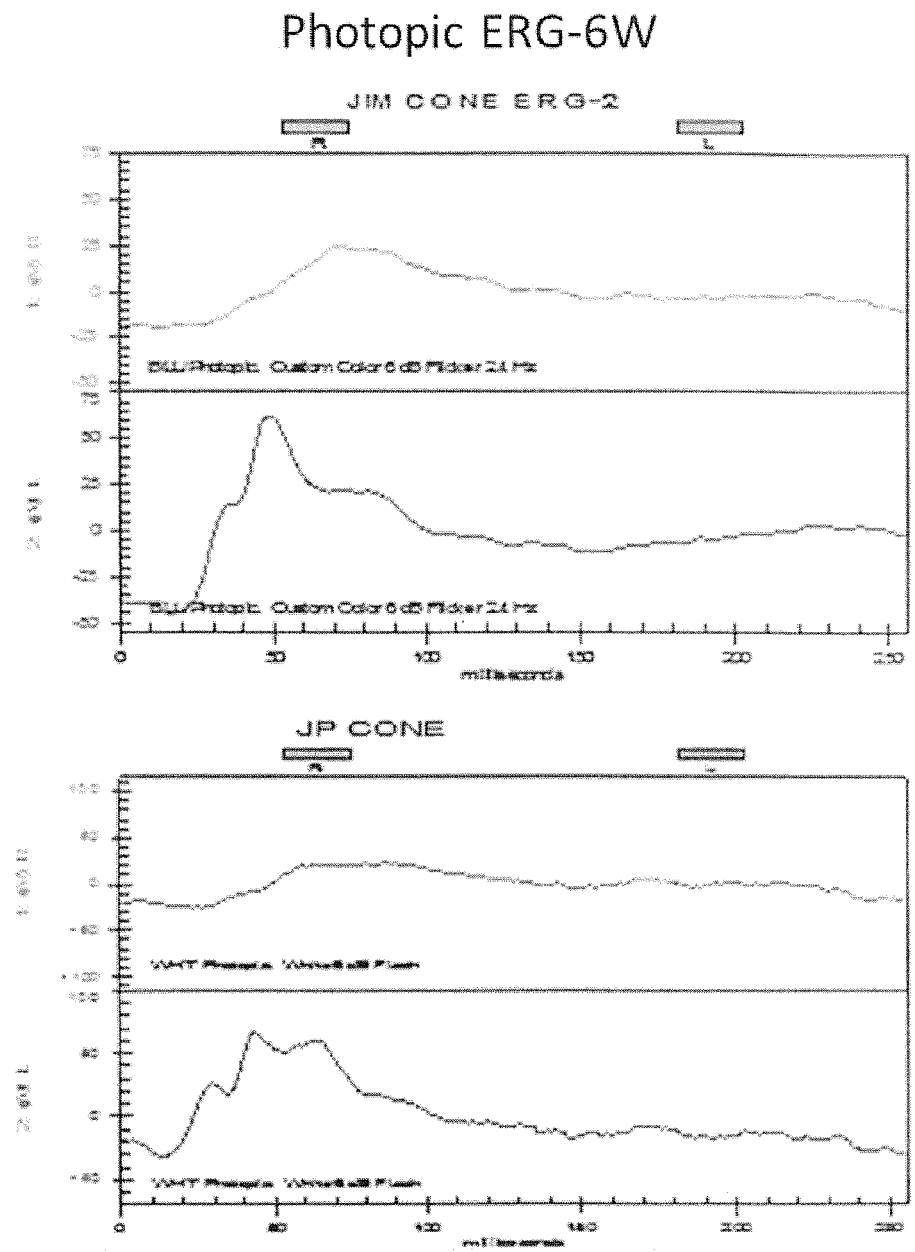
Figure 9C:
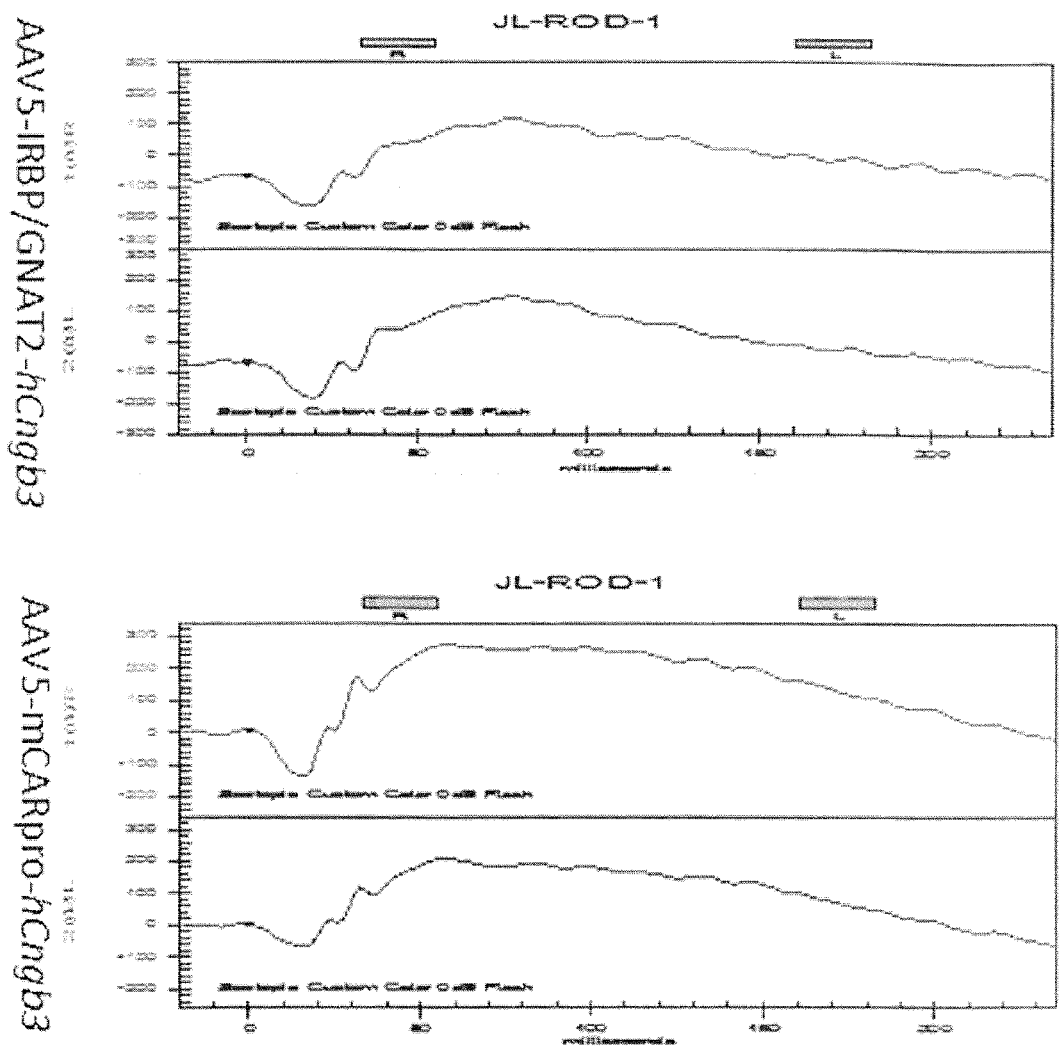
Figure 9D:
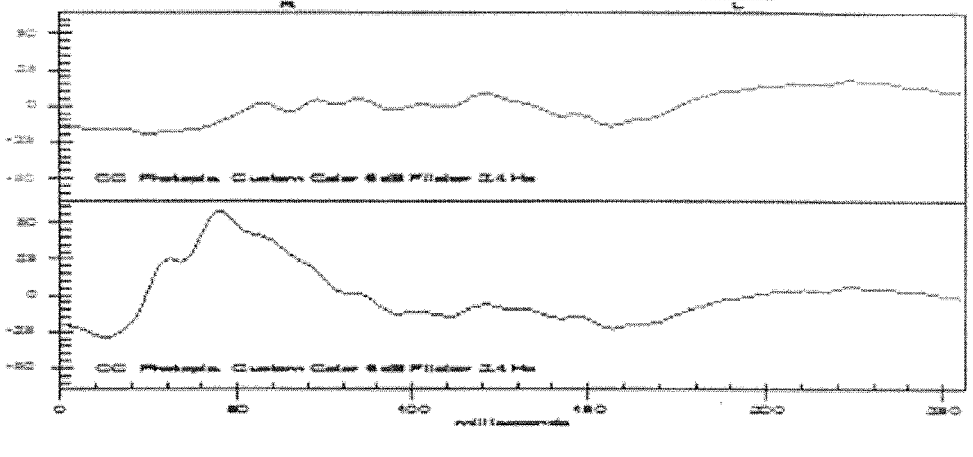
Figure 9D:
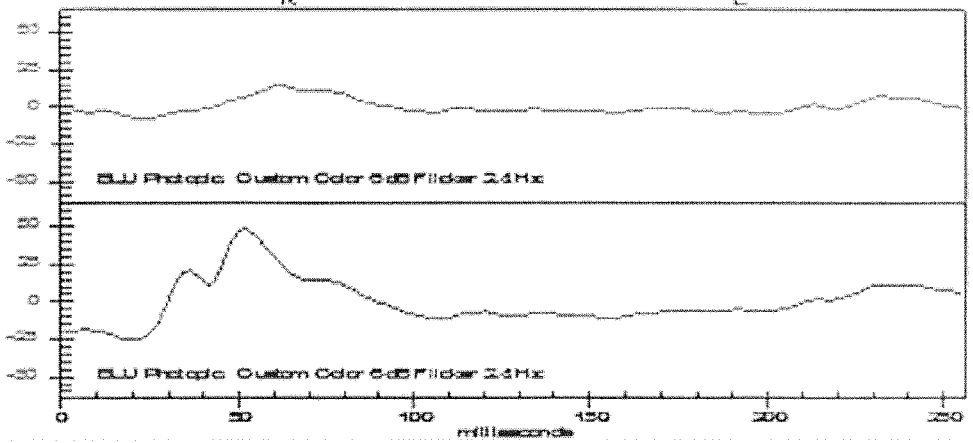
Figure 10A:
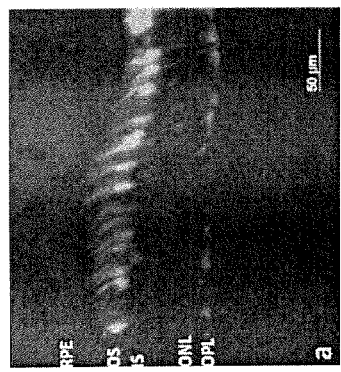
FIGS. 10A-10C. GFP reporter gene expression mediated by AAV5 containing a IRBP/GNAT2 promoter.
Figure 10B:
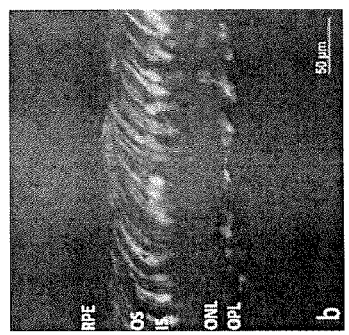
Figure 10C:
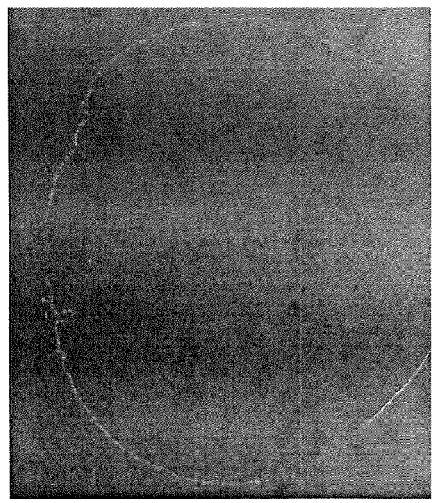

Results: At 3 weeks post-treatment both treated and untreated eyes of Cngb3 knockout mice showed normal rod-derived ERGs. In untreated control eyes, cone-derived ERG signals were nearly unrecordable. In both AAV5-mCAR-hCngb3 and AAV5-IRBP/GNAT2-hCngb3 treated eyes, restored light-adapted cone-derived ERG waveforms were first recorded 3 weeks after treatment and remained stable for at least 6 months (FIGS. 9A-9D). ERG amplitudes were about ⅔ of those of normal uninjected C57BL/6J mice. Immunohistochemistry showed human CNGB3 staining in the outer segments of many cones in treated eyes but not in cones from partner untreated eyes (FIGS. 7A-7C). Anti-M-cone or S-cone opsin staining also showed that S-opsins were preserved in treated eyes but not in untreated eyes of Cngb3 knockout mice (FIGS. 8A and 8B).

Conclusions: Both AAV5-mCAR-hCNGB3 and AAV5-IRBP/GNAT2-hCNGB3 restore cone function and prevent S-cone degeneration for at least 6 months in Cngb3 knockout mice, a model of ACHM 1. However additional experiments show that in addition to cones, mCAR-pro also expresses its transgene in the RPE while the IRBP/GNAT2 promoter is cone-exclusive (see FIGS. 11A and 11B). Thus, the IRBP/GNAT2 promoter is preferable for use in humans.

TABLE 3

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

TABLE 1

Summary of results of AAV cone targeting experiments.

| Promoter names | Source | Expression pattern in rodent | Expression pattern in dog | Expression pattern in primate | size | References/Studies |
| --- | --- | --- | --- | --- | --- | --- |
| PR 2.1 | Human red green opsin promoter | All cones, some rods Expression strong | Only L/M cones Expression strong | Only L/M cones Expression strong | 2100 bps | Alexander et al. 2007, Komaromy et al. 2008, Komaromy et al. 2010 and Mancuso et al. 2009 |
| HB569 | (HB569) human blue cone opsin promoter | M and S cones and rods Expression weak | Few L/M cones, rods and RPE Expression weak | Not tested | 570 bps and | Glushakova et al. 2006, Komaromy et al. 2008 and Komaromy et al. 2010 |
| mBP | (mBP) mouse blue cone promoter | | | | 500 bps | Michalakis et al. 2010 |
| hCAR | (hCAR) Human cone arrestin promoter | All cones, some rods and RPE Expression strong | All cones, rods and some RPE Expression strong | Not tested | 500 bps and | Li et al. 2002 and Carvalho et al. 2011 |
| mCAR | (mCAR) mouse cone arrestin promoter | | | | 500 bps | Hauswirth and Komaromy unpublished results |

TABLE 2

Summary of AAV5-IRBP/GNAT2-hGFP transduction.

| Promoter names | Source | Expression pattern in rodent | Expression pattern in dog | Expression pattern in primate | size | References/Studies |
| --- | --- | --- | --- | --- | --- | --- |
| IRBP/GNAT2 | Human IRBP gene and human GNAT2 gene | All cones, some rods Expression strong | Cones only, L/M and S cones Expression strong | Not tested | 524 bps | Not published |

REFERENCES

U.S. Pat. No. 5,986,174
U.S. Pat. No. 6,080,914
U.S. Pat. No. 6,106,826
U.S. Pat. No. 6,165,781
U.S. Pat. No. 6,204,251
U.S. Pat. No. 6,461,606
U.S. Pat. No. 6,660,514
U.S. Pat. No. 7,094,604

Gene Therapy: Principles and Applications, Springer Verlag 1999.

Alexander J J, Umino Y, Everhart D, Chang B, Min S H, Li Q, Timmers A M, Hawes N L, Pang J J, Barlow R B, Hauswirth W W. Restoration of cone vision in a mouse model of achromatopsia. Nat Med. 2007 June; 13(6):685-7.

Carvalho L S, Xu J, Pearson R A, Smith A J, Bainbridge J W, Morris L M, Fliesler S J, Ding X Q, Ali R R. Long-teen and age-dependent restoration of visual function in a mouse model of CNGB3-associated achromatopsia following gene therapy. Hum Mol Genet. 2011 Jun. 13.

Daniele L L, Lillo C, Lyubarsky A L, Nikonov S S, Philp N, Mears A J, Swaroop A, Williams D S, Pugh EN Jr. Cone-like morphological, molecular, and electrophysiological features of the photoreceptors of the Nrl knockout mouse. Invest Ophthalmol Vis Sci. 2005 June; 46(6):2156-67

Fong S L, Criswell M H, Belecky-Adams T, Fong W B, McClintick J N, Kao W W, Edenberg H J. Characterization of a transgenic mouse line lacking photoreceptor development within the ventral retina. Exp Eye Res. 2005 October; 81(4):376-88.

Glushakova L G, Timmers A M, Pang J, Teusner J T, Hauswirth WW. Human blue-opsin promoter preferentially targets reporter gene expression to rat s-cone photoreceptors. Invest Ophthalmol Vis Sci. 2006 August; 47(8): 3505-13.

Komáromy A M, Alexander J J, Rowlan J S, Garcia M M, Chiodo V A, Kaya A, Tanaka J C, Acland G M, Hauswirth W W, Aguirre G D. Gene therapy rescues cone function in congenital achromatopsia. Hum Mol Genet. 2010 Jul. 1; 19(13):2581-93.

Komáromy A M, Alexander J J, Cooper A E, Chiodo V A, Glushakova L G, Acland G M, Hauswirth W W, Aguirre G D. Targeting gene expression to cones with human cone opsin promoters in recombinant AAV. Gene Ther. 2008 July; 15(14):1049-55. Epub 2008 Mar. 13.

Li A, Zhu X, Craft C M. Retinoic acid upregulates cone arrestin expression in retinoblastoma cells through a Cis element in the distal promoter region. Invest. Ophthalmol. Vis. Sci. 2002; 43:1375-1383.

Mancuso K, Hauswirth W W, Li Q, Connor T B, Kuchenbecker J A, Mauck M C, Neitz J, Neitz M. Gene therapy for red-green colour blindness in adult primates. Nature. 2009 Oct. 8; 461(7265):784-7.

Mears, A. J., M. Kondo, P. K. Swain, Y. Takada, R. A. Bush, T. L. Saunders, P. A. Sieving, and A. Swaroop. 2001. Nrl is required for rod photoreceptor development. Nat. Genet. 29:447-452.

Michalakis S, Malfriedel R, Tanimoto N, Krishnamoorthy V, Koch S, Fischer M D, Becirovic E, Bai L, Huber G, Beck S C, Fahl E, Burling H, Paquet-Durand F, Zong X, Gollisch T, Biel M, Seeliger M W. Restoration of cone vision in the CNGA3−/− mouse model of congenital complete lack of cone photoreceptor function. Mol Ther. 2010 December; 18(12):2057-63.

Nikonov S S, Daniele L L, Zhu X, Craft C M, Swaroop A, Pugh EN Jr. Photoreceptors of Nrl−/− mice coexpress functional S- and M-cone opsins having distinct inactivation mechanisms. J Gen Physiol. 2005 March; 125(3):287-304.

Pang J J, Alexander J, Lei B, Deng W, Zhang K, Li Q, Chang B, Hauswirth W W. Achromatopsia as a potential candidate for gene therapy. Adv Exp Med Biol. 2010; 664:639-46.

Ying S, Fong S L, Fong W B, Kao C W, Converse R L, Kao WW. A CAT reporter construct containing 277 bp GNAT2 promoter and 214 bp IRBP enhancer is specifically expressed by cone photoreceptor cells in transgenic mice. Curr Eye Res. 1998 August; 17(8):777-82.

Ying S, Jansen H T, Lehman M N, Fong S L, Kao W W. Retinal degeneration in cone photoreceptor cell-ablated transgenic mice. Mol Vis. 2000 Jun. 24; 6:101-8.

Beltz, G. A., Jacobs, K. A., Eickbush, T. H., Cherbas, P. T., Kafatos, F. C. (1983) "Isolation of multigene families and determination of homologies by filter hybridization methods" *Methods of Enzymology*, R. Wu, L. Grossman and K. Moldave [eds.] Academic Press, New York 100:266-285.

Maniatis, T., Fritsch, E. F., Sambrook, J. (1982) *Molecular Cloning: A Laboratory Manual*, Cold Spring Harbor Laboratory, Cold Spring Harbor, N.Y.

Altschul, S. F. et al. (1990) "Basic Local Alignment Search Tool" *J. Mol. Biol.* 215:403-410.

Altschul, S. F. et al. (1997) "Gapped BLAST and PSI-BLAST: A New Generation of Protein Database Search Programs" *Nucl. Acids Res.* 25:3389-3402.

Karlin S., Altschul, S. F. (1990) "Methods for Assessing the Statistical Significance of Molecular Sequence Features by Using General Scoring Schemes" *Proc. Natl. Acad. Sci. USA* 87:2264-2268.

Karlin S., Altschul, S. F. (1993) "Applications and Statistics for Multiple High-Scoring Segments in Molecular Sequences" *Proc. Natl. Acad. Sci. USA* 90:5873-5877.

Feigner, P. L., T. R. Gadek, M. Holm, R. Roman, H. W. Chan, M. Wenz, J. P. Northrop, G. M. Ringold, M. Danielsen (1987) "Lipofection: a highly efficient, lipid-mediated DNA-transfection procedure" *Proc Natl Acad Sci U.S.A.* 84(21):7413-7417.

We claim:

1. A polynucleotide that promotes expression in cone cells of an operably linked nucleotide sequence, wherein said polynucleotide comprises an enhancer nucleotide sequence of an interphotoreceptor retinoid-binding protein (IRBP) gene sequence that is positioned upstream of a promoter nucleotide sequence of a cone transducing alpha-subunit (GNAT2) gene sequence, wherein said polynucleotide sequence comprises the nucleotide sequence shown in SEQ. ID NO:1 or SEQ. ID NO:4.

2. The polynucleotide according to claim 1, wherein said polynucleotide further comprises a nucleotide sequence encoding a therapeutic protein or a functional protein or a reporter protein.

3. The polynucleotide according to claim 2, wherein said polypeptide is a cyclic nucleotide-gated (CNG) channel polypeptide.

4. The polynucleotide according claim 3, wherein said CNG polypeptide is a CNGA3 or a CNGB3 polypeptide.

5. The polynucleotide according to claim 4, wherein said CNG3B polypeptide comprises the amino acid sequence of SEQ ID NO:5.

* * * * *